US009446410B2

(12) United States Patent
Evans et al.

(10) Patent No.: US 9,446,410 B2
(45) Date of Patent: Sep. 20, 2016

(54) THERMAL CYCLER APPARATUS WITH ELASTOMERIC ADHESIVE

(75) Inventors: Zackery Kent Evans, Woods Cross, UT (US); Thomas Knight Bodily, Salt Lake City, UT (US); Richard David Abbott, Draper, UT (US); Patrick L. Riley, Salt Lake City, UT (US)

(73) Assignee: BIOFIRE DEFENSE, LLC, Salt Lake City, UT (US)

( * ) Notice: Subject to any disclaimer, the term of this patent is extended or adjusted under 35 U.S.C. 154(b) by 194 days.

(21) Appl. No.: 13/989,344

(22) PCT Filed: Dec. 2, 2011

(86) PCT No.: PCT/US2011/063005
§ 371 (c)(1),
(2), (4) Date: Jul. 9, 2013

(87) PCT Pub. No.: WO2012/075360
PCT Pub. Date: Jun. 7, 2012

(65) Prior Publication Data

US 2014/0051155 A1 Feb. 20, 2014

Related U.S. Application Data

(60) Provisional application No. 61/419,680, filed on Dec. 3, 2010.

(51) Int. Cl.
*B01L 7/00* (2006.01)
*C12M 3/00* (2006.01)

(52) U.S. Cl.
CPC .............. *B01L 7/52* (2013.01); *B01L 2200/12* (2013.01); *B01L 2200/147* (2013.01);
(Continued)

(58) Field of Classification Search
CPC ................ B01L 7/52; B01L 2200/12; B01L 2200/147; B01L 2300/023; B01L 2300/024; B01L 2300/046; B01L 2300/16; B01L 2300/1822; B01L 2300/1894; B01L 2300/027; Y10T 156/1057
See application file for complete search history.

(56) References Cited

U.S. PATENT DOCUMENTS 6,197,572 B1 3/2001 Schneebeli
6,337,435 B1 1/2002 Chu et al.
(Continued)

FOREIGN PATENT DOCUMENTS

CN 2842313 11/2006
CN 101194021 6/2008
(Continued)

OTHER PUBLICATIONS

International Search Report for PCT/US2011/063005 dated Apr. 3, 2012.
(Continued)

*Primary Examiner* — Gautam Prakash
(74) *Attorney, Agent, or Firm* — Workman Nydegger

(57) ABSTRACT

An apparatus for thermal cycling can transfer heat uniformly and efficiently. The apparatus can be used in a method that reduces condensation on sample wells. The apparatus can also be manufactured to provide uniform configurations. For example, a sample, illustratively for polymerase chain reaction (PCR), in each sample well and the components of the embodiment of the thermal cycler apparatus shown at including a well block, a base plate, a layer of adhesive, a peltier device, another layer of adhesive and a heat sink.

29 Claims, 30 Drawing Sheets

(52) U.S. Cl.
CPC ... *B01L 2300/023* (2013.01); *B01L 2300/024* (2013.01); *B01L 2300/027* (2013.01); *B01L 2300/046* (2013.01); *B01L 2300/16* (2013.01); *B01L 2300/1822* (2013.01); *B01L 2300/1894* (2013.01); *Y10T 156/1057* (2015.01)

(56) References Cited

U.S. PATENT DOCUMENTS

| | | | | |
|---|---|---|---|---|
| 7,387,887 | B2 | 6/2008 | Wittwer et al. | |
| 2003/0008308 | A1* | 1/2003 | Enzelberger et al. | 435/6 |
| 2006/0094108 | A1 | 5/2006 | Yoder et al. | |
| 2006/0286659 | A1 | 12/2006 | Atwood et al. | |
| 2008/0138887 | A2 | 6/2008 | Atwood et al. | |
| 2009/0130719 | A1* | 5/2009 | Handique | 435/91.2 |
| 2009/0263782 | A1 | 10/2009 | Ward et al. | |
| 2010/0081191 | A1 | 4/2010 | Woods | |

FOREIGN PATENT DOCUMENTS

| | | |
|---|---|---|
| JP | 2001241761 | 9/2001 |
| JP | 2002010775 | 1/2002 |
| JP | 2006224060 | 8/2006 |
| JP | 2009537152 | 10/2009 |
| JP | 2009278971 | 12/2009 |
| WO | 2008030914 | 3/2008 |
| WO | 2008070198 | 6/2008 |
| WO | 2012075360 | 6/2012 |

OTHER PUBLICATIONS

Singapore Search Report and Written Opinion based on Application No. 2013042734 dated Feb. 22, 2016.

* cited by examiner

THERMAL CYCLER APPARATUS WITH ELASTOMERIC ADHESIVE

This application claims the benefit of and priority to PCT Application Serial No. PCT/US2011/063005, filed 2 Dec. 2011, entitled "THERMAL CYCLER APPARATUS AND RELATED METHODS", which also claims the benefit of and priority to U.S. Provisional Patent Application Ser. No. 61/419,680, entitled "THERMAL CYCLER APPARATUS AND RELATED METHODS", filed 3 Dec. 2010 with inventors Zackery Kent Evans, Thomas Knight Bodily, Richard David Abbott and Patrick L. Riley, the entirety of which is incorporated herein by reference.

TECHNICAL FIELD

The present disclosure relates generally to an apparatus for thermal cycling. Certain embodiments relate more specifically to a method of manufacturing an apparatus and a method of using the apparatus.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
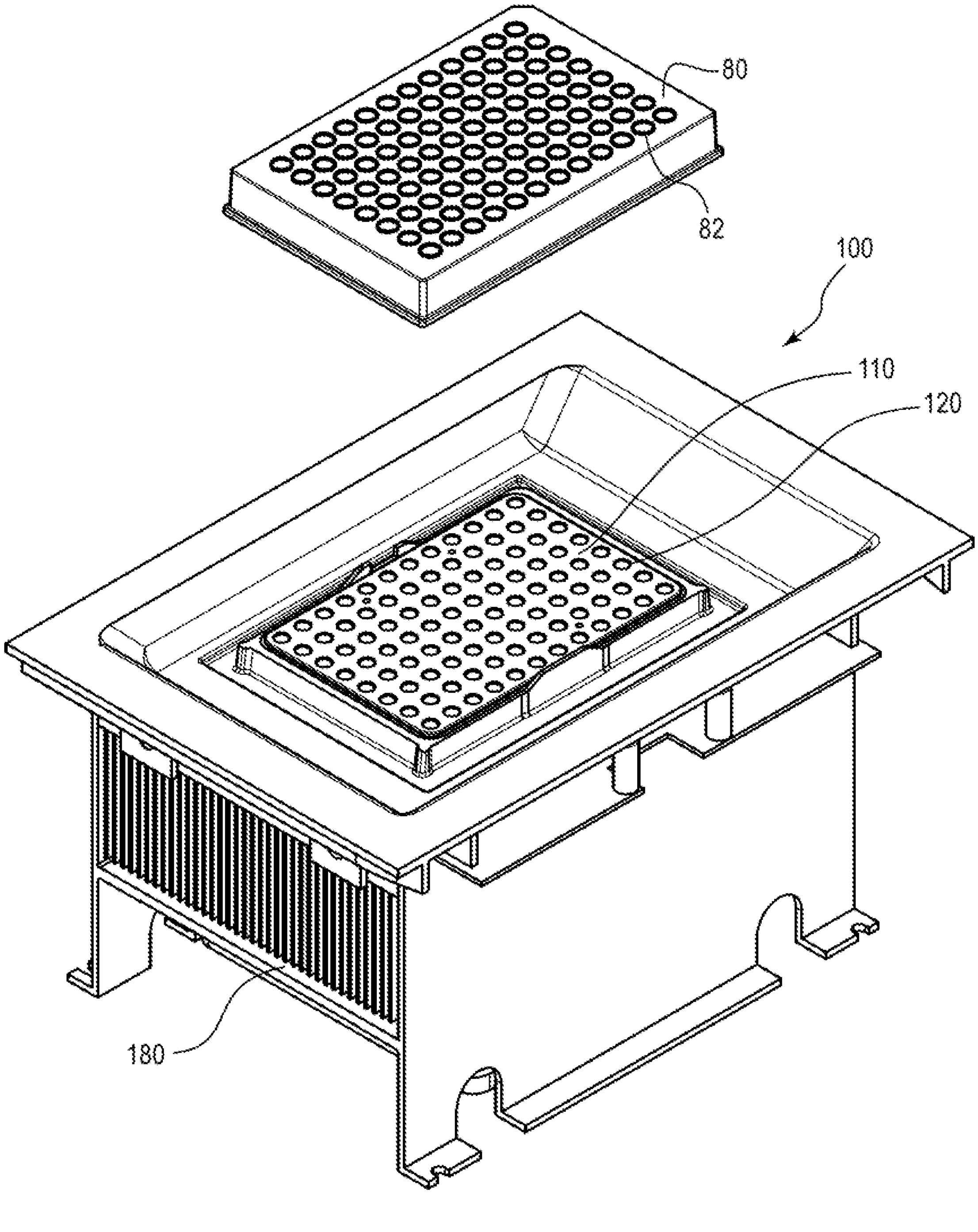
FIG. 1 is a perspective view of a sample plate above a thermal cycler apparatus.
Figure 2:
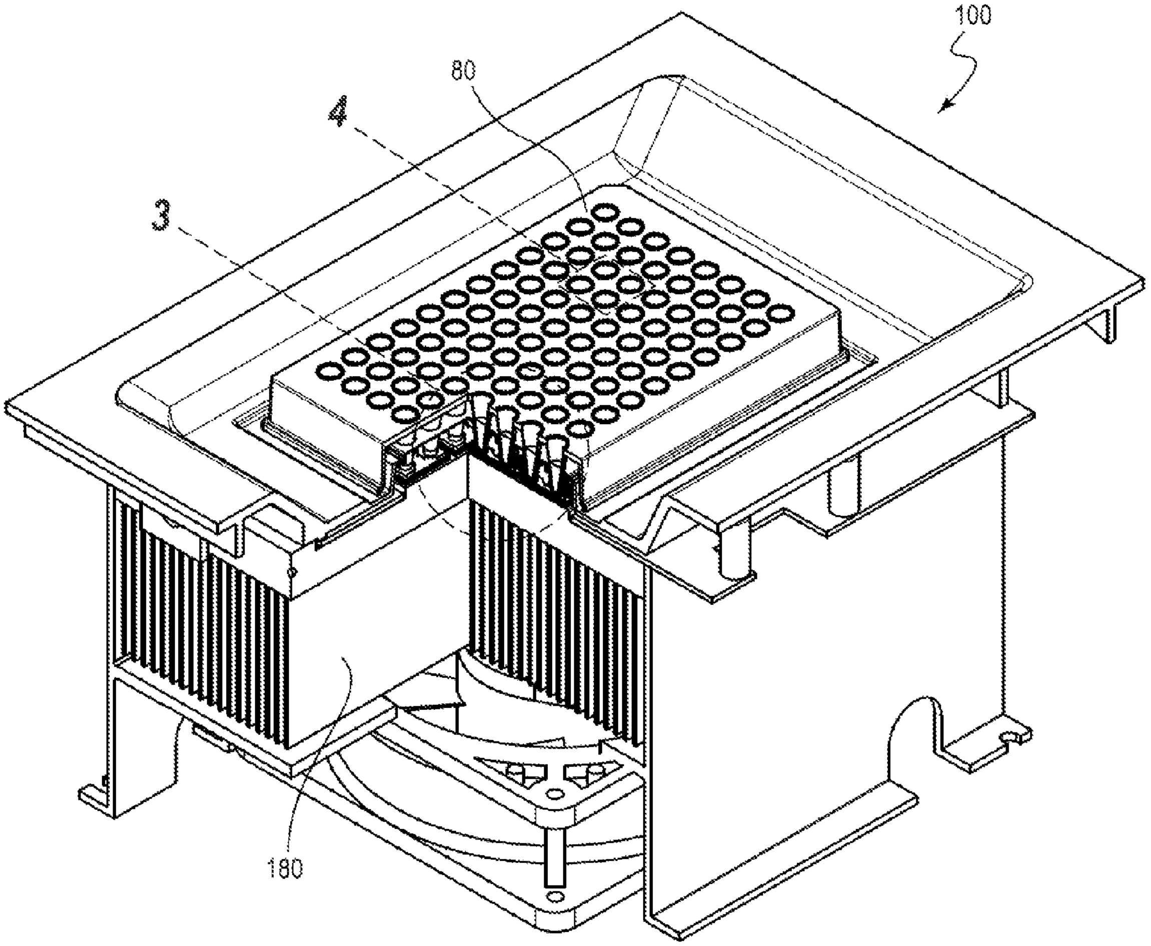
FIG. 2 is a perspective view of the sample plate on a thermal cycler apparatus with a partial cut-away view.
Figure 3:
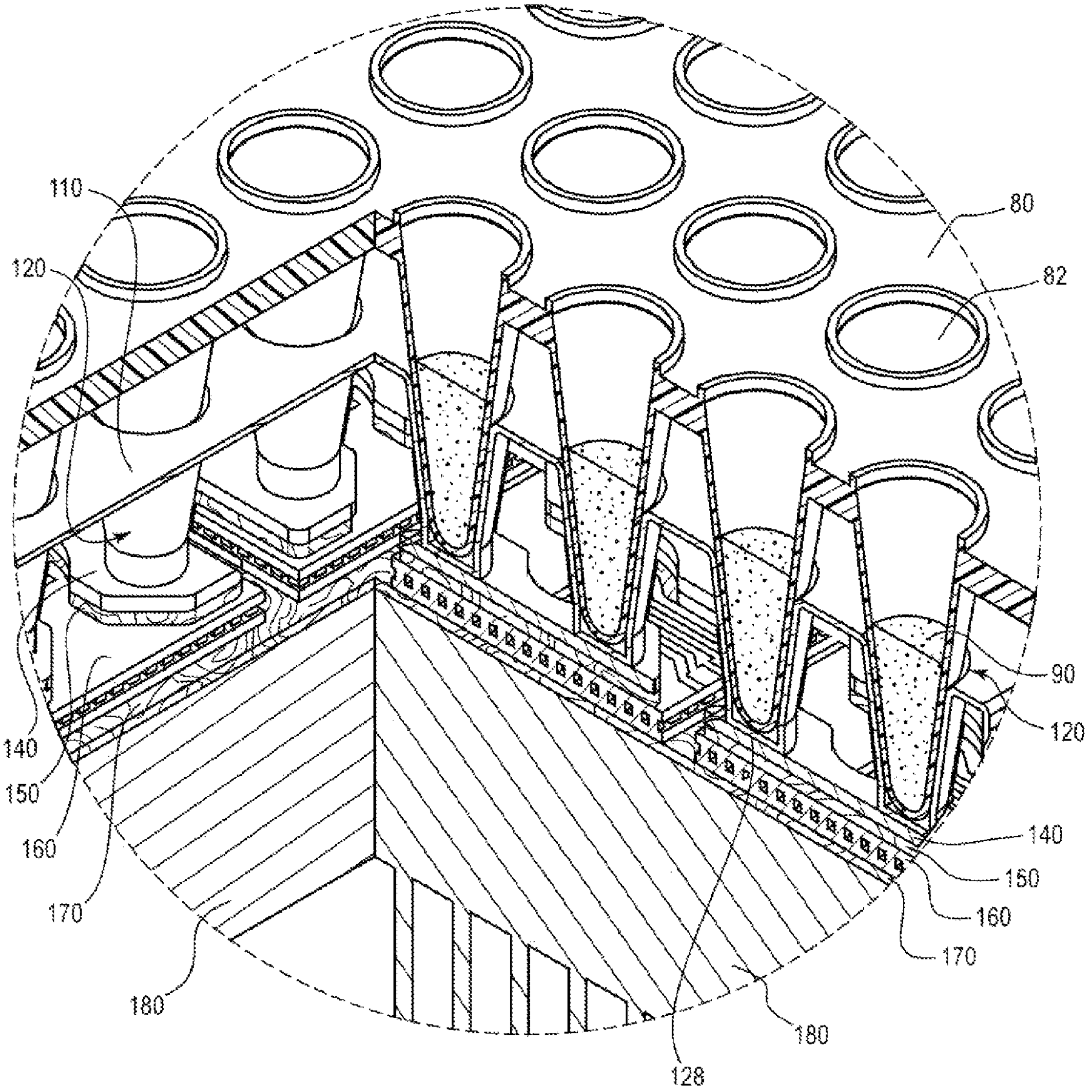
FIG. 3 is a cross-sectional view of the sample plate on the thermal cycler apparatus taken along cutting line 3-3 in FIG. 2.
Figure 4:
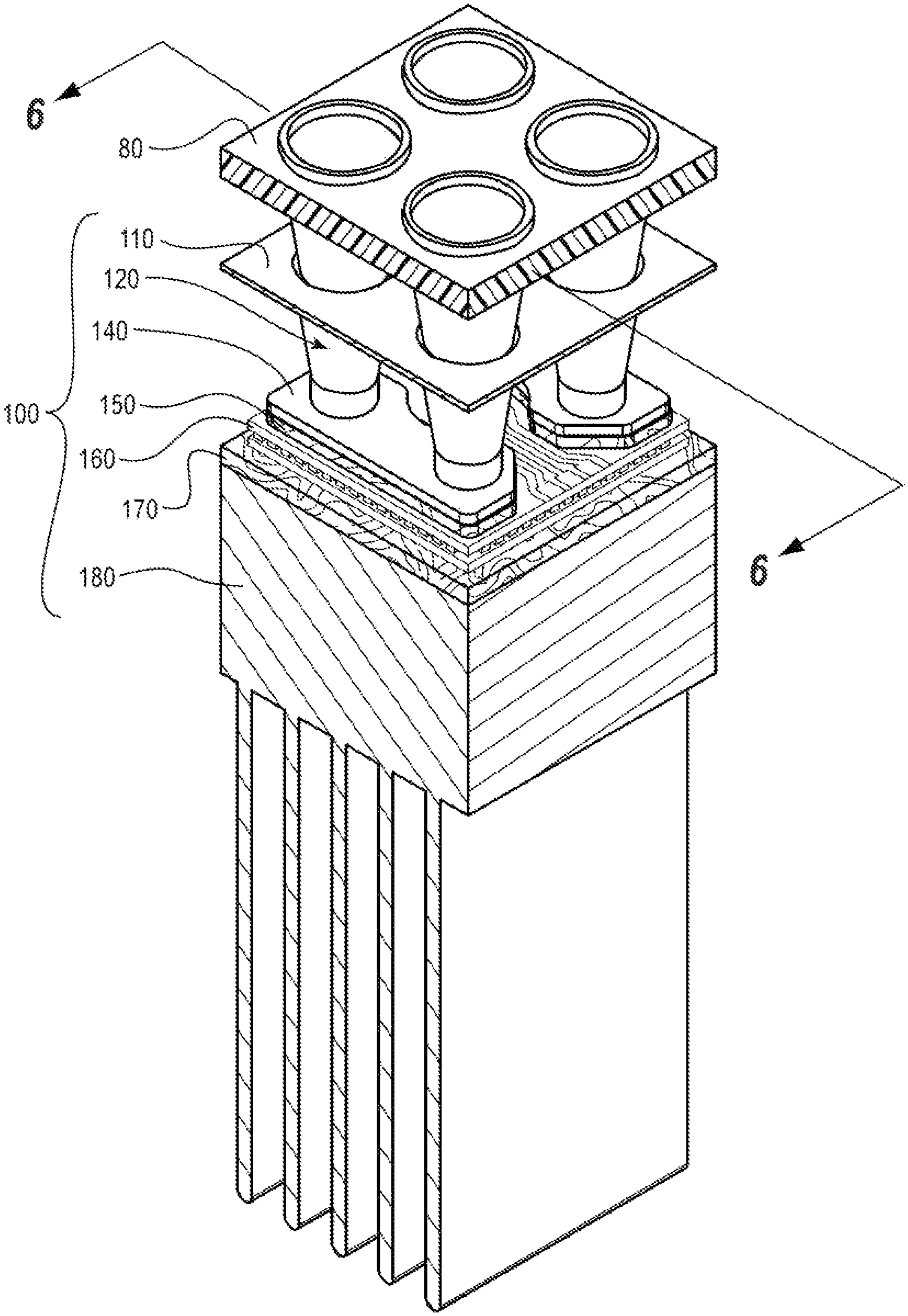
FIG. 4 is an isolated sectional view taken along cutting line 4-4 in FIG. 2 of the thermal cycler apparatus.
Figure 5:
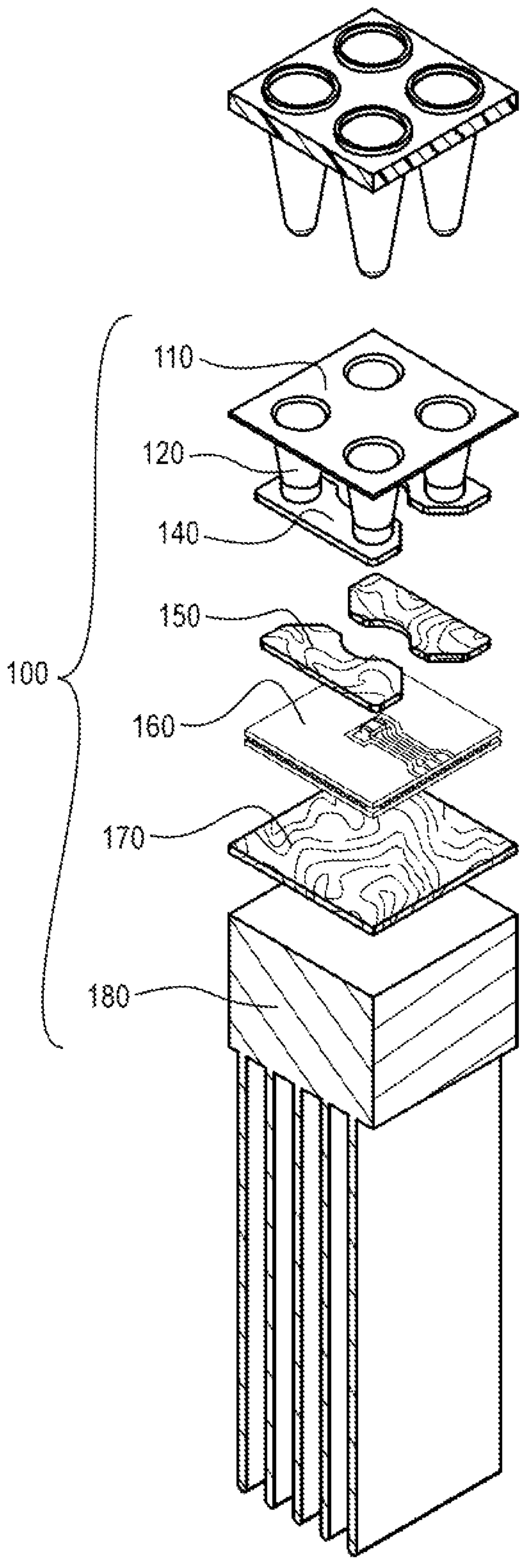
FIG. 5 is an exploded perspective of the sections shown in FIG. 4 of the sample plate on the thermal cycler apparatus.
Figure 6:
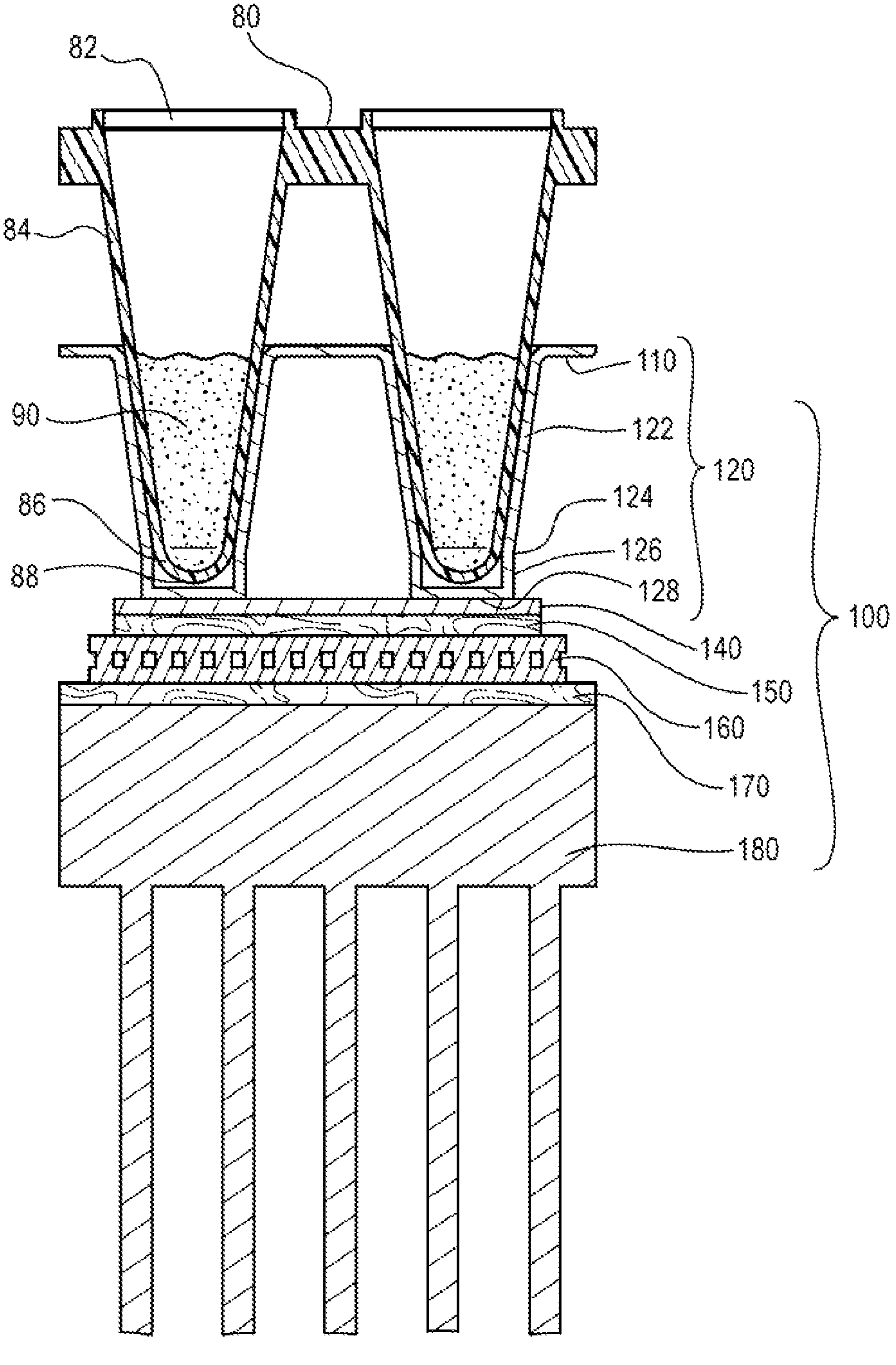
FIG. 6 is a cross-sectional side view taken along cutting line 6-6 in FIG. 4 of the embodiment of the thermal cycler apparatus and sample plate that are shown in FIGS. 1-5.

FIG. 1 shows a sample plate 80 with sample wells 82 ready to be positioned on a well block 110 of a thermal cycler apparatus 100 such that each sample well 82 is positioned in a well 120 of well block 110. FIG. 2 shows the same components after sample plate 80 is positioned on thermal block plate 110. The configuration of thermal cycler apparatus 100 can be appreciated by studying FIGS. 3-6. FIG. 3 is an enlarged view of the cut-away provided in FIG. 2. FIGS. 4-6 provided isolated sectional views taken along cutting line 4-4 in FIG. 2 of the sample plate on the thermal block plate. FIG. 3 and FIG. 6 show a sample 90, illustratively for PCR, in each sample well 82 and the components of the embodiment of the thermal cycler apparatus shown at 100 including a well block 110, a base plate 140, a layer of adhesive 150, a peltier device 160, another layer of adhesive 170 and a heat sink 180. As shown in FIGS. 3-6, well block 110 extends roughly half way up side wall 84 of sample well 82. However, this is exemplary only and it is understood that other well block heights are within the scope of this invention, such as the tall well block 110' shown in FIG. 7. The exploded perspective of the components shown in FIG. 5 provides the most insightful view as it can be seen that there is a pair of base plates 140 for each 4-well zone, and each pair spans between two adjacent wells. It can also be seen in FIG. 5 that the layer of adhesive 150 provides an interface with peltier device 160. Additionally, it can be seen that peltier device 160 is thermally coupled to the pair of base plates 140 via the layer of adhesive 150.

More detail regarding the plurality of wells 120 of well block 110 can be seen in FIG. 6. Well 120 is shown having an upper conical sidewall 122, a transitional sidewall 124, a lower cylindrical sidewall 126 and a bottom 128 that is flat and extends between lower cylindrical sidewall 126. Flat bottom 128 rests on base plate 140, which rests on adhesive 150 to be thermally coupled to peltier plate 160. FIG. 6 also shows more details about the configuration of sample well 82 including sidewall 84, rounded bottom-section 86 of well 82 and the round apex 88.

The layers of adhesive 150 and 170 may be the same material. The adhesive is ductile and flexible, has relatively high thermal conductivity and low viscosity. Illustratively, the adhesive enhances the uniformity of heat transfer between peltier 160 and wells 120. In one embodiment, the adhesive permits apparatus 100 to be assembled without the use of conventional clamps used to clamp a well block to a heat sink. When an adhesive is used in an embodiments such as apparatus 100, the adhesive is capable of retaining the peltier device 160 adjacent to the structure contacted by the adhesive such as the wells 120 of well block 110 and/or heat sink 180 even when apparatus 100 is turned upside down without clamping well block 110 to heat sink 180.

Various embodiments of a suitable adhesive are capable of cycling between a temperature at least as high as 95° C. and at least as low as 60° C. at least about 5,000 times, at least about 10,000 times, at least about 100,000 times, or at least about 200,000 times and still be capable of retaining peltier device 160. Various embodiments of a suitable adhesive may have an elongation, as defined below in the Examples, of at least about 15%, 20%, 22%, 35%, 40%, 50%, 55%, 60%, 70%, 90%, 110%, 120%, 180%, 200%, 400% or ranges within combinations of these values such as about 15% to about 1,000%, about 35% to about 700%, about 70% to about 500%, or between 100% to about 200%.

Suitable adhesives may also have an unprimed adhesion lap shear of between about 1 kgf/cm$^2$ and about 75 kgf/cm$^2$, over about 10 kgf/cm$^2$, between about 10 kgf/cm$^2$ and about 45 kgf/cm$^2$. The viscosity of the adhesive may range between about 1,000 centipoise and about 200,000 centipoise, between about 10,000 centipoise and about 150,000 centipoise, between about 20,000 centipoise and about 80,000 centipoise, or between about 30,000 centipoise and about 40,000 centipoise.

Various embodiments may also have a thermal conductivity, as defined below in the Examples, of at least about 0.39, 0.40, 0.74, 0.77, 0.84, 0.85, 0.9, 0.92, 0.95, 1.1, 1.4, 1.53, 1.8, 1.9, 1.97, 2.2, 2.5 or ranges within combinations of these values such as about 0.74 to about 2.5 or about 0.9 to about 1.8. In one embodiment, the adhesive has a thermal conductivity at 25° C./77° F. of between about 0.7 Watt/meter-K and about 2.5 Watt/meter-K. In another embodiment, the adhesive has a thermal conductivity at 25° C./77° F. of between about 0.8 Watt/meter-K and about 2.0 Watt/meter-K. In one embodiment, the adhesive has a thermal conductivity at 25° C./77° F. of between about 0.9 Watt/meter-K and about 1.5 Watt/meter-K. In yet another embodiment, the adhesive has a thermal conductivity at 25° C./77° F. of over about 1.0 Watt/meter-K. In a further embodiment, the polymer has a thermal conductivity at 25° C./77° F. of about 1.1 Watt/meter-K.

Examples of suitable adhesives include thermally conductive silicone pastes, which are non-curing. Specific trade names of suitable thermally conductive silicone pastes, which are non-curing, are provided by those listed in the Examples.

Figure 7:
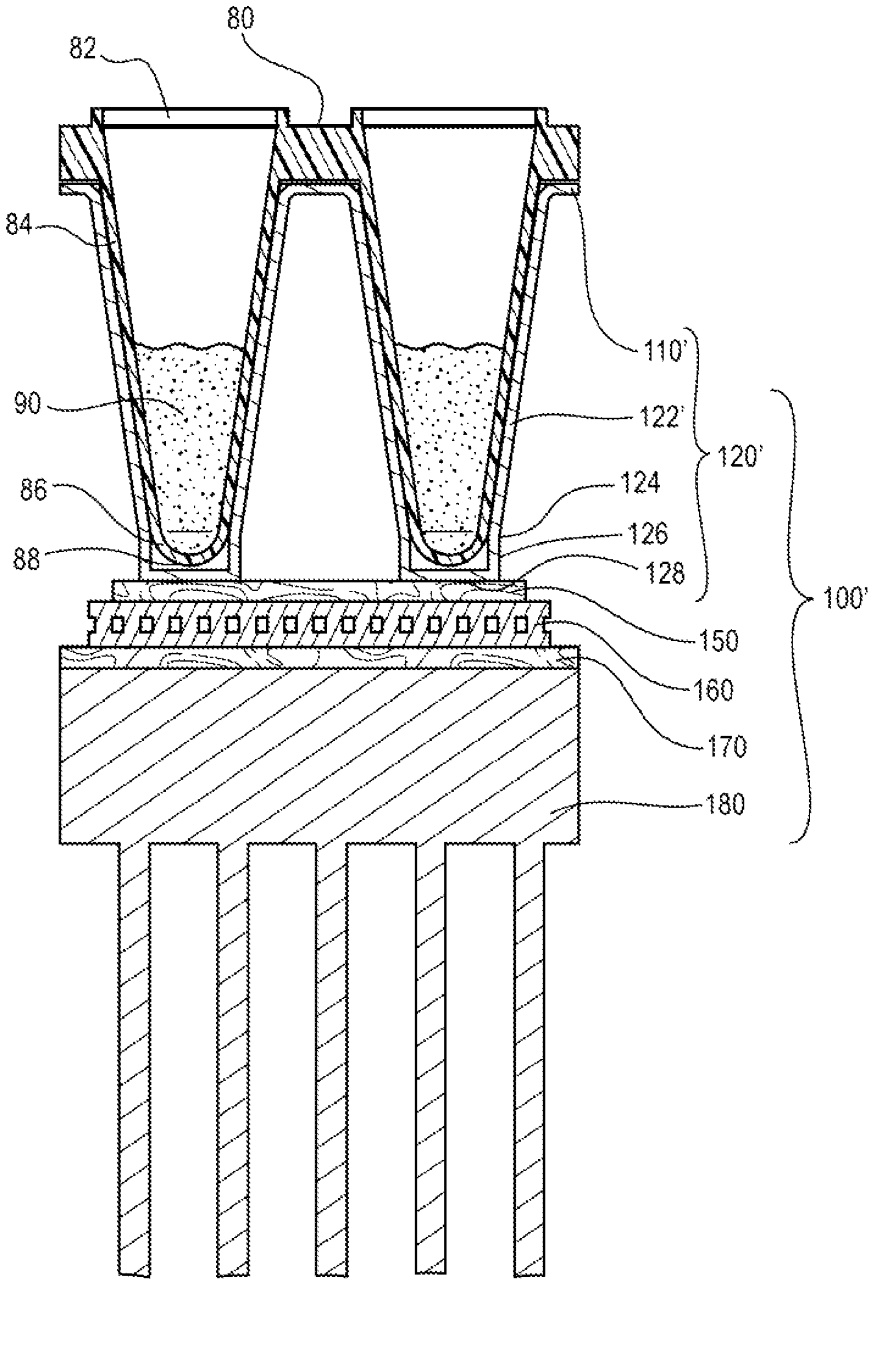
FIG. 7 is a cross-sectional side view of a different embodiment of thermal cycler apparatus.

The embodiment depicted in FIG. 7 of a thermal cycler apparatus at 100' differs from apparatus 100 as apparatus 100' does not have base plates such as base plate 140. Also, apparatus 100' features a well block 110' having wells 120' with taller side walls 122'. The embodiments of the well blocks disclosed herein may each have such taller side walls instead of side walls 122 or side walls 422. Wells 120' have flat bottoms 128 that are directly over and in contact with a layer of adhesive 150. While the configuration of apparatus 100' provides less area for layer of adhesive 150 to bond to relative to the configuration of apparatus 100, the configuration of apparatus 100' also permits faster heat transfer between peltier device 160 and wells 120' as there is less mass for the heat to pass through without a base plate.

Figure 8A:
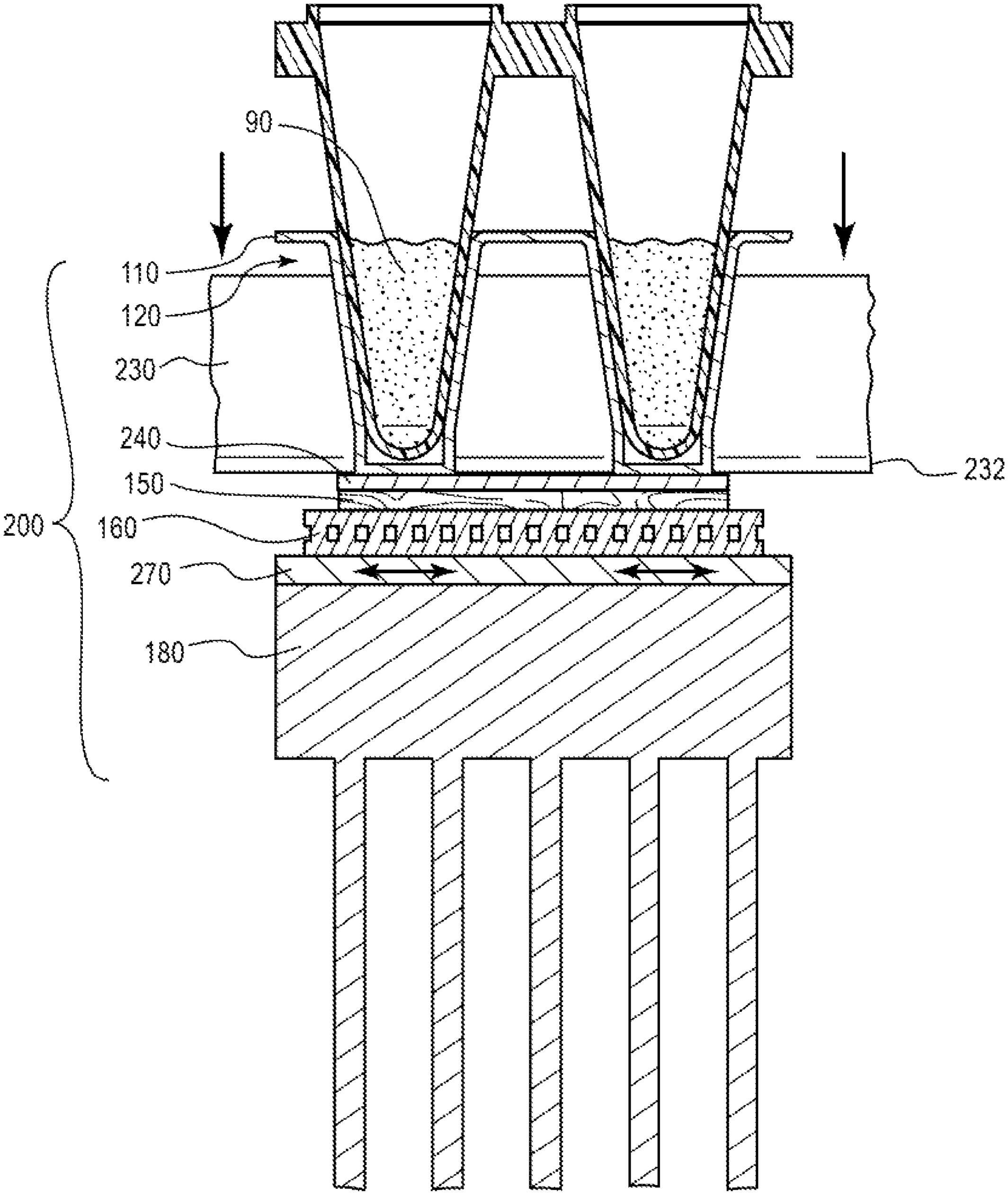
FIG. 8A is a cross-sectional side view of another embodiment of a thermal cycler apparatus.
Figure 8B:
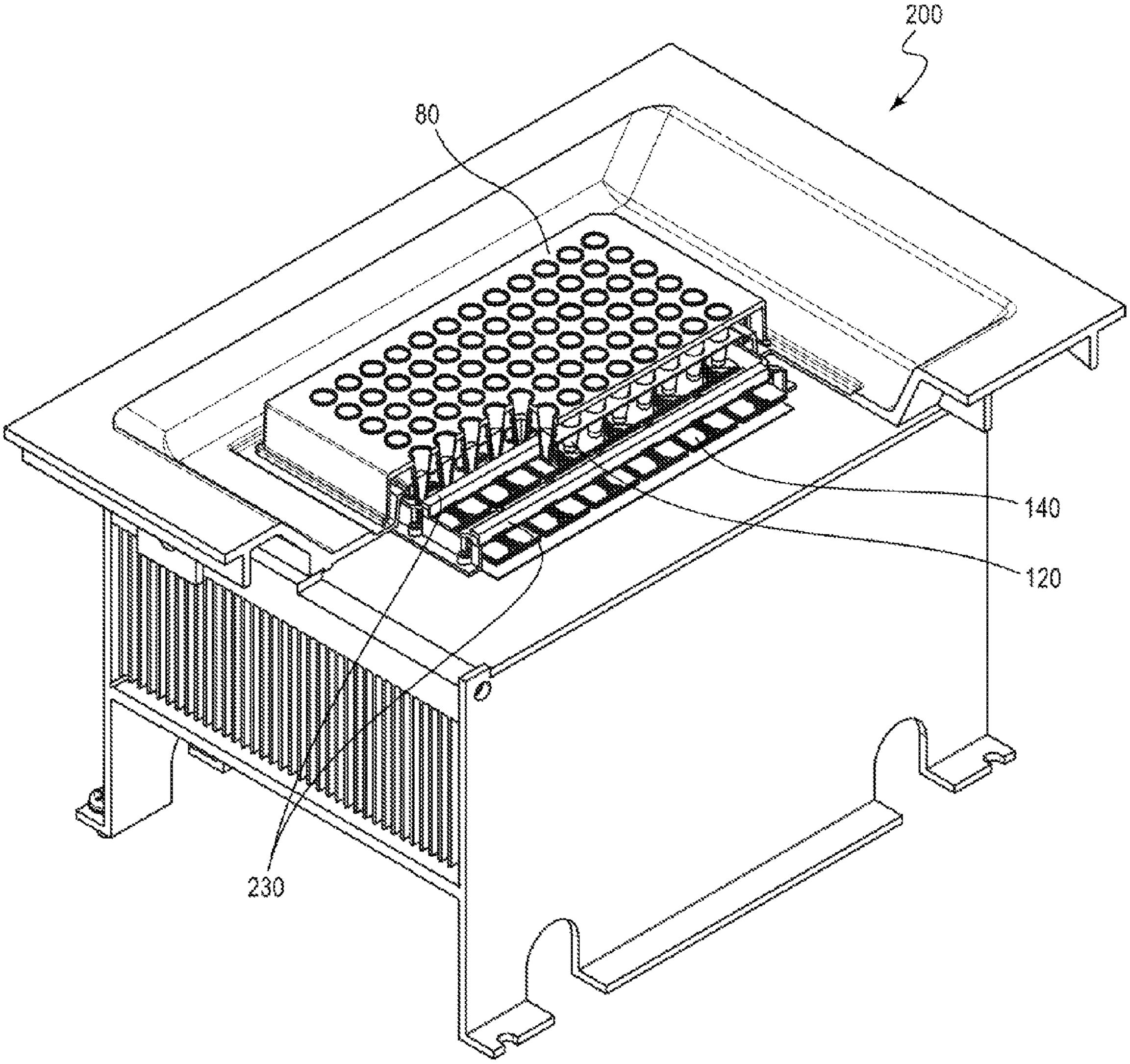
FIG. 8B is a perspective view of the embodiment of a thermal cycler apparatus shown in FIG. 8A with a cross-sectional view to show a clamp.

FIGS. 8A-8B depicts another embodiment of a thermal cycler apparatus at 200. Apparatus 200 features a carbon sheet or grease or other non-binding thermal interface material at 270 instead of an adhesive. Optionally, the non-binding thermal interface material 270 may also replace the layer of adhesive 150. Because carbon sheet or grease does not retain peltier device 160 adjacent to heat sink 180 when apparatus 100' is turned upside down, it is necessary to clamp well block 110 to heat sink 180 with a clamp bar 230. Clamp bar 230 may alternatively rest on a thin compression pad or compliant layer 232 that may be formed from a suitable material such as silicone. Clamp bar 230 extends across adjacent base plates 140 and can be attached at its ends with conventional mechanisms for clamp systems to the apparatus 200. It is also possible use clamp screws that extend through the well block and into the heat sink. Various clamp bar and clamp screw embodiments are known in the art.

Figure 9:
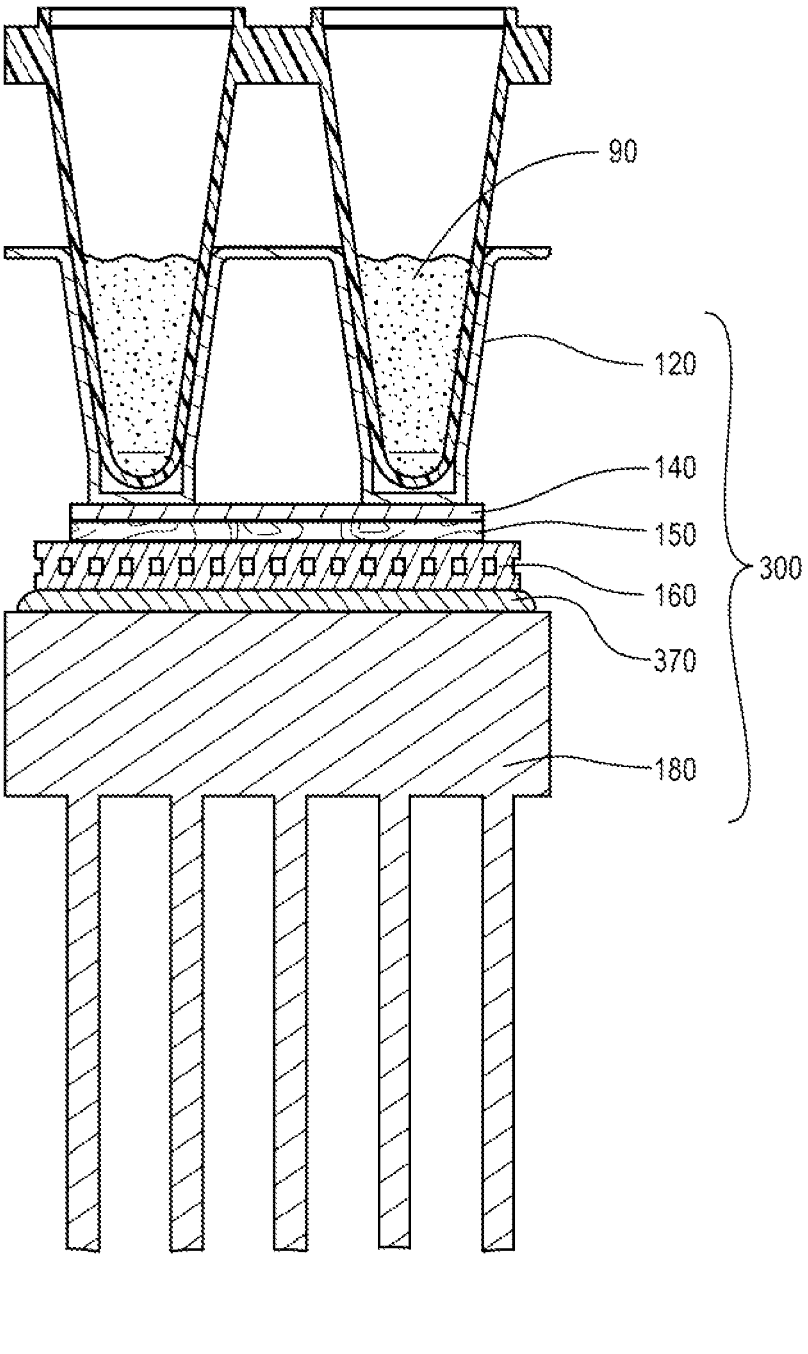
FIG. 9 is a cross-sectional side view of an additional embodiment of a thermal cycler apparatus.

FIG. 9 depicts another embodiment of a thermal cycler apparatus at 300. Apparatus 300 features solder 370 between peltier device 160 and heat sink 180. As with the embodiments shown in FIGS. 6-7, with this configuration, it is also not necessary for well block 110 to be clamped to heat sink 180.

Figure 10:
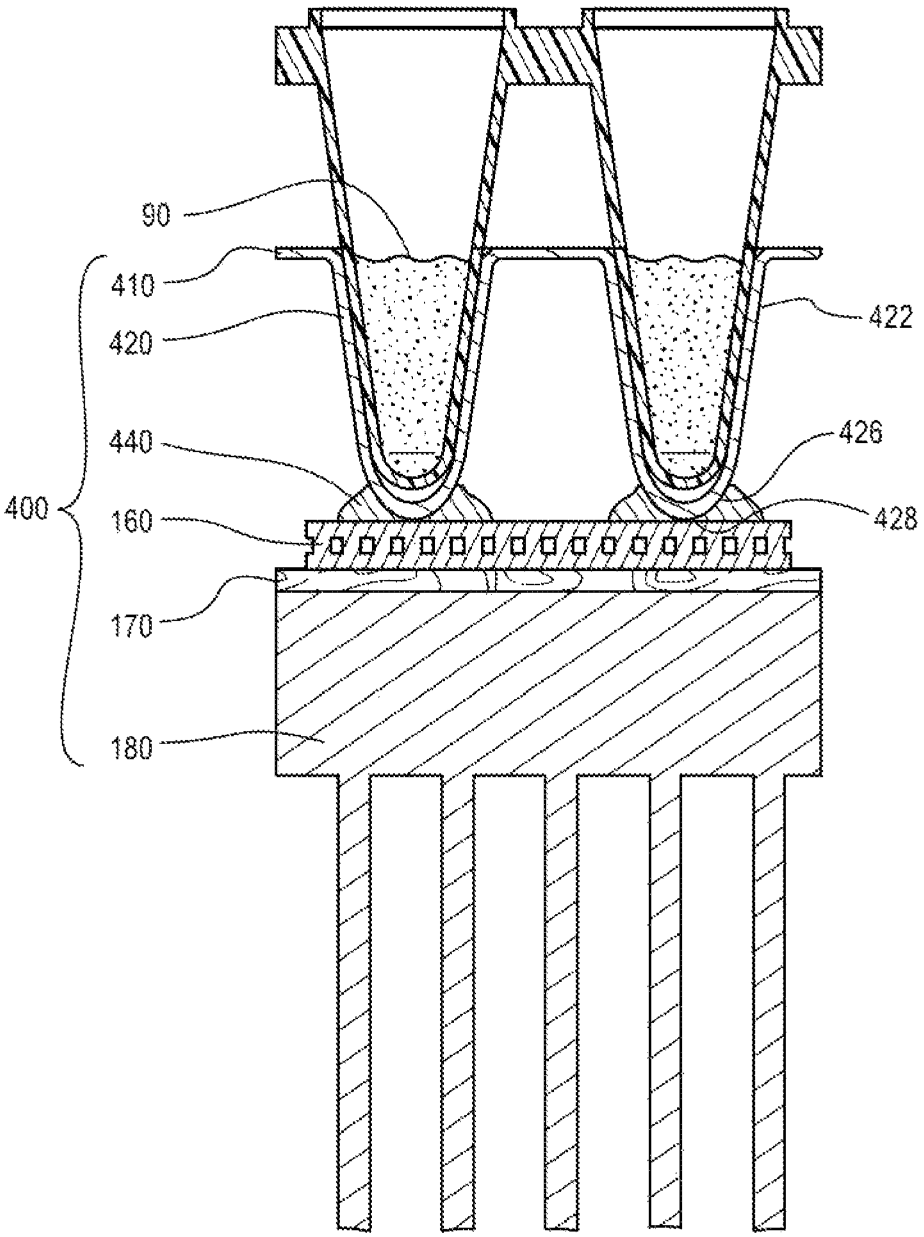
FIG. 10 is a cross-sectional side view of another embodiment of a thermal cycler apparatus.

FIG. 10 depicts another embodiment of a thermal cycler apparatus at 400. Apparatus 400 features a well block 410 with wells 420 that have sidewalls 422, which transition to rounded bottoms 426 and have a rounded apex 428 instead of a flat bottom. Also, the rounded bottom of each well 420 rests in solder 440 illustratively with rounded apex 428 directly contacting peltier device 160. Wells with flat bottoms such as wells 120 can also be soldered like wells 420 directly to a peltier device, as shown in FIG. 7.

Figure 11:
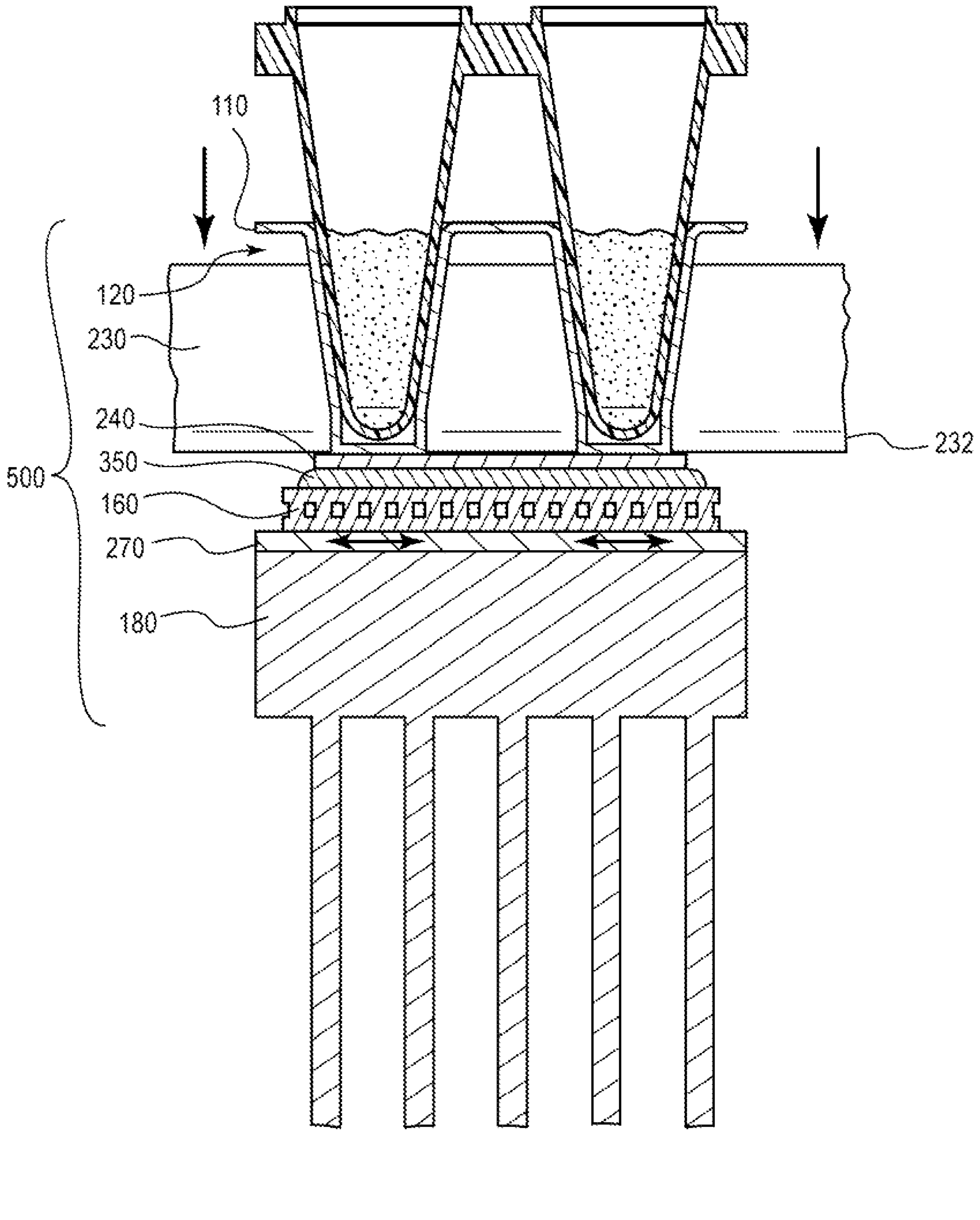
FIG. 11 is a cross-sectional side view of yet another embodiment of a thermal cycler apparatus.

FIG. 11 depicts another embodiment of a thermal cycler apparatus at 500. Apparatus 500 features well block 110, on base plate 240, which is soldered to peltier device 160 via solder 350. Peltier device 160 rests on non-binding thermal interface material 270 so clamp bar 230 is also used with the same configuration as described above with respect to apparatus 200. In addition to the apparatuses discussed above and depicted at 100, 100', 200, 300, 400 and 500, other combinations may also be used. For example, apparatus 500 can be modified by replacing solder 350 with adhesive 150 or with non-binding thermal interface material 270 such as carbon or grease.

Figure 12:
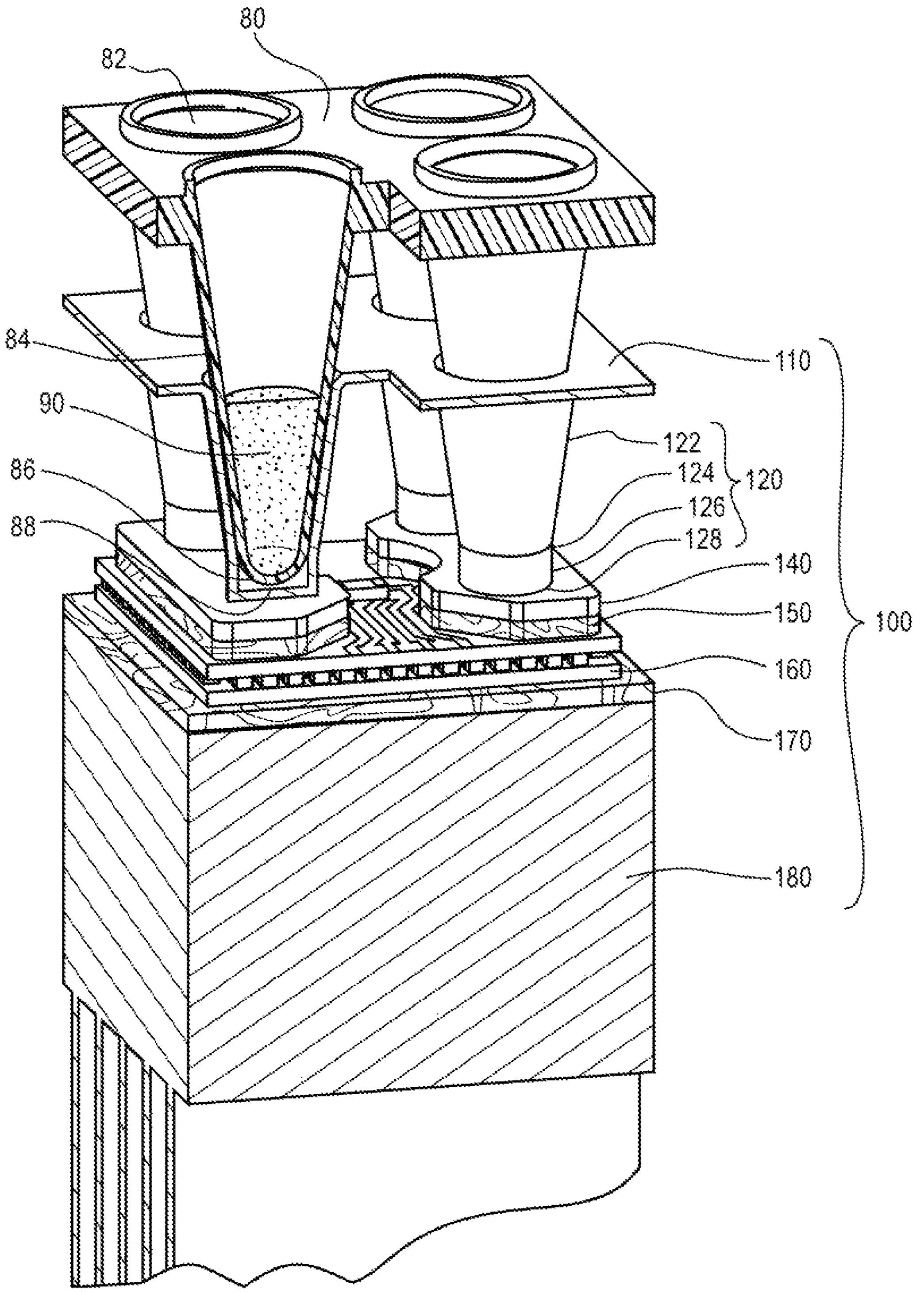
FIG. 12 is a cross-sectional side view of the embodiment of the thermal cycler apparatus and sample plate shown in FIGS. 1-5 that shows the configuration of the thermal block plate.

FIG. 12 corresponds with the embodiment shown in FIGS. 1-6 and shows all of the components of a single zone. Apparatus 100 has a well block 110 that comprises a plurality of 4-well zones, wherein each 4-well zone comprises a first pair of wells 120 and a second pair of wells 120, and wherein each first pair of wells 120 and each second pair of wells 120 are respectively over a first base plate and a second base plate such that one peltier device 160 provides for heat transfer for one 4-well zone. Each peltier device 160 heats or cools a pair of base plates 140 via adhesive 150 to heat or cool the sample in the four sample wells via each bottom 128 and side walls 122 of the four wells 120. Heat sink 180 is thermally connected to peltier device 160 via adhesive 170. It is understood that the 4-well zone is illustrative only, and that each zone may comprise various other numbers of wells.

Figure 13:
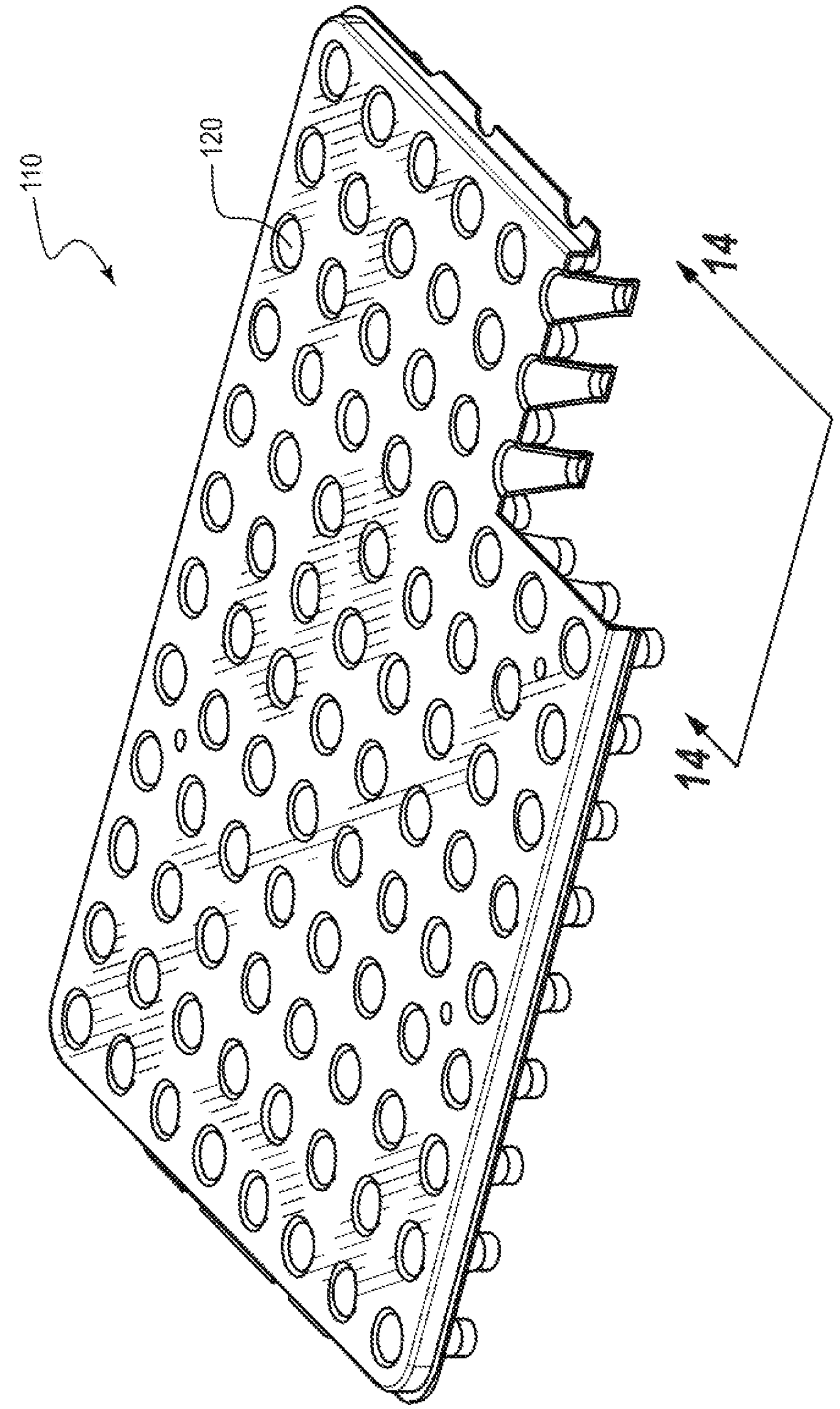
FIG. 13 is a perspective view of the well block shown in FIG. 1.
Figure 14:
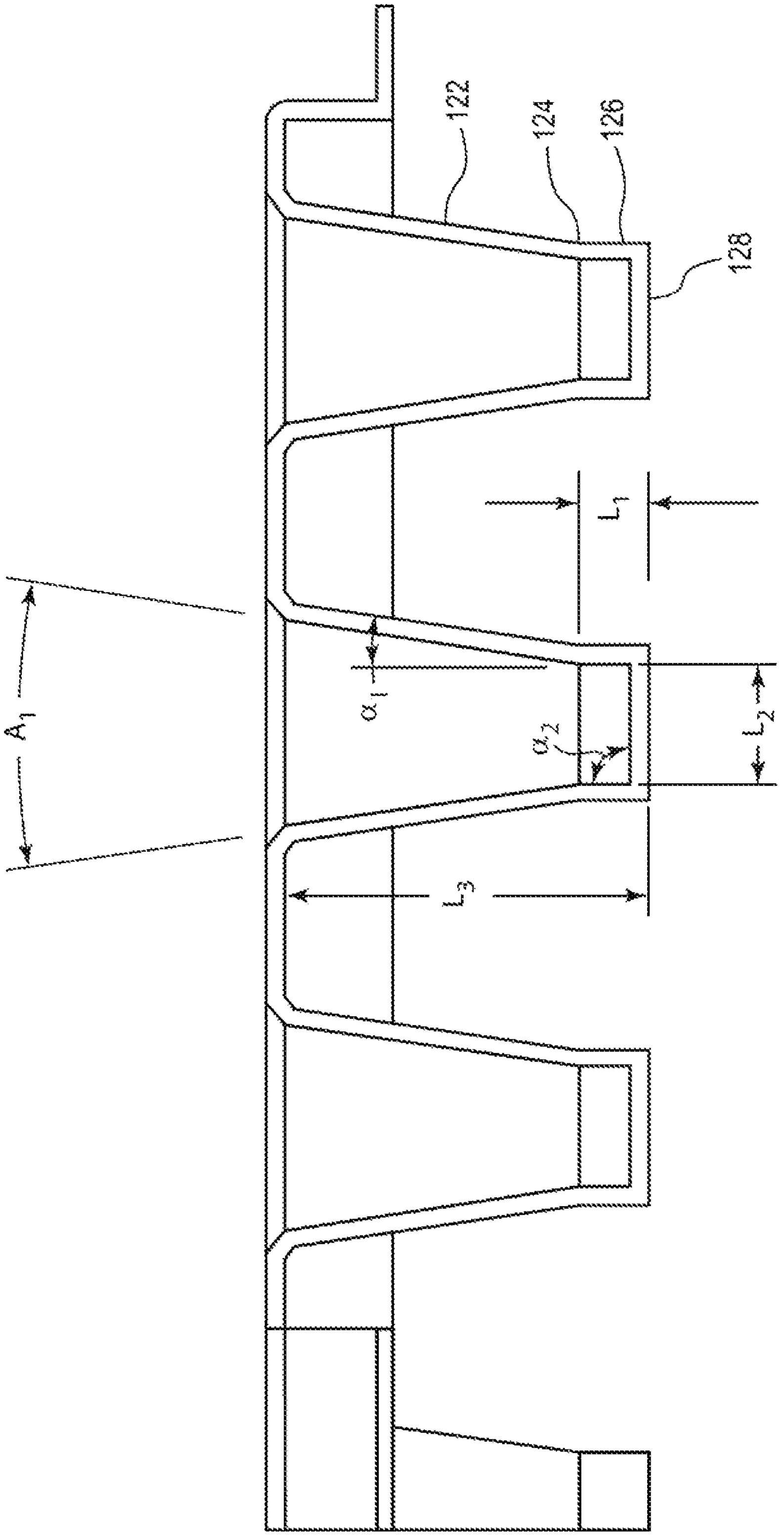
FIG. 14 is a cross-sectional side view of the well block taken along cutting line 14-14 in FIG. 13.

More detailed information about the configuration of well 120 can be appreciated with reference to FIGS. 12-14. FIG. 14 provides references for describing the dimensions of well 120. The length of lower cylindrical sidewall 126 is identified as $L_1$, the diameter of flat bottom 128 is identified as $L_2$, and the depth of well 120 is identified as $L_3$, and the angle between the upper conical sidewall 122 and a line extending from the lower cylindrical sidewall 126 is identified as $\alpha_1$. The angle, $\alpha_1$, between the upper conical sidewall 122 and the lower cylindrical sidewall 126 in one embodiment is about 16°, such as 16.3°, however other angles are within the scope of this invention and may approximately correspond to external dimensions of commercially available microtiter plates. The angle, $\alpha_2$, between the lower cylindrical sidewall 126 and flat bottom 128 is equal to or slightly greater than 90°, such as 92°, however other angles are within the scope of this invention. While a 90° angle $\alpha_2$ is contemplated, angles slightly greater than 90° may be desired, illustratively to ease removal of well block 110 from the mold used in the manufacturing process. It is understood that if angles slightly greater than 90° for $\alpha_2$ are used, that cylindrical sidewall 126 will define a generally cylindrical section that is, in fact, slightly conical. Illustratively, $\alpha_2$ is less than $90°+\alpha_1$, illustratively 95° degrees or less, and more illustratively, 92° or less.

An advantage of flat bottom 128 relative to prior art configurations is that the shape can be manufactured with greater uniformity, and provides additional surface area that enables heat to be transferred with greater uniformity and at a more rapid rate. However, it is understood that flat bottom 128 may have rounded edges near sidewall 126 or otherwise may not be completely flat from one side of cylindrical sidewall 126 to the other. Moreover, because lower cylindrical sidewall 126 does not interfere with insertion of the sample well 82 into well 120, the shape of the well 120 allows sample well 82 to have maximal contact with the sidewall 122 of the wells in each well block.

An average well 120' of well block 110', as shown in FIG. 7, is close to the height of sample well 82 and illustratively has a depth of about 0.5 inches-0.6 inches for a 96-well plate. Such a well block allows sample well 82 to be filled with a large sample volume and also mitigates against the effects of a heated lid that may be at a static temperature. Most embodiments illustrated in this disclosure, including in FIGS. 1-6, 8-17, 20-22, and 25, have a depth of well 120, $L_3$, that is shorter, illustratively only about 0.3 inches for a 96-well plate. An advantage of this configuration is a decrease in the incidence of sidewall condensation, particularly during cooling. Due to reduced well height relative to a convention well, another advantage of this configuration is a decrease in well block mass relative to prior art configuration, which increases the thermal cycling rate. It is understood that the choice of height of the wells of the well block depends on the specific application and that either configuration may be used with the various embodiments disclosed herein.

Figure 15A:
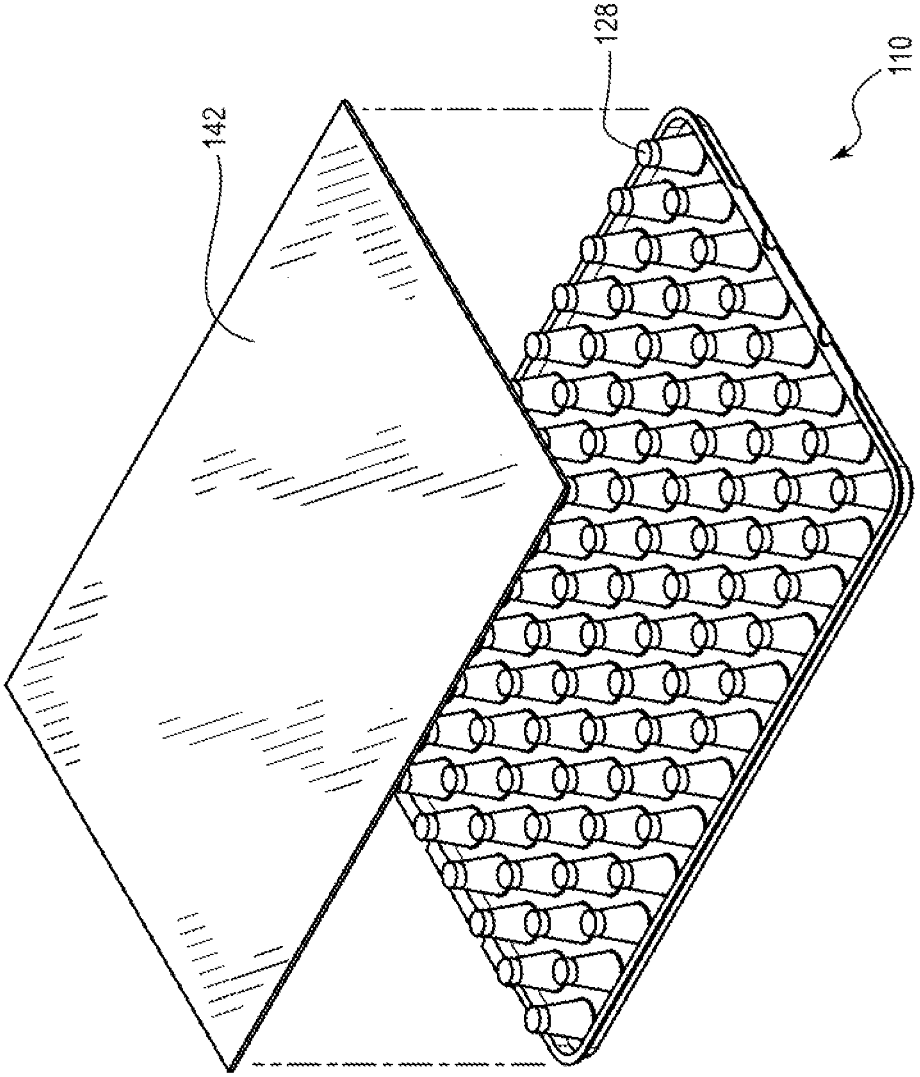
FIG. 15A is a perspective view of the well block and a base plate before they are joined together.
Figure 15B:
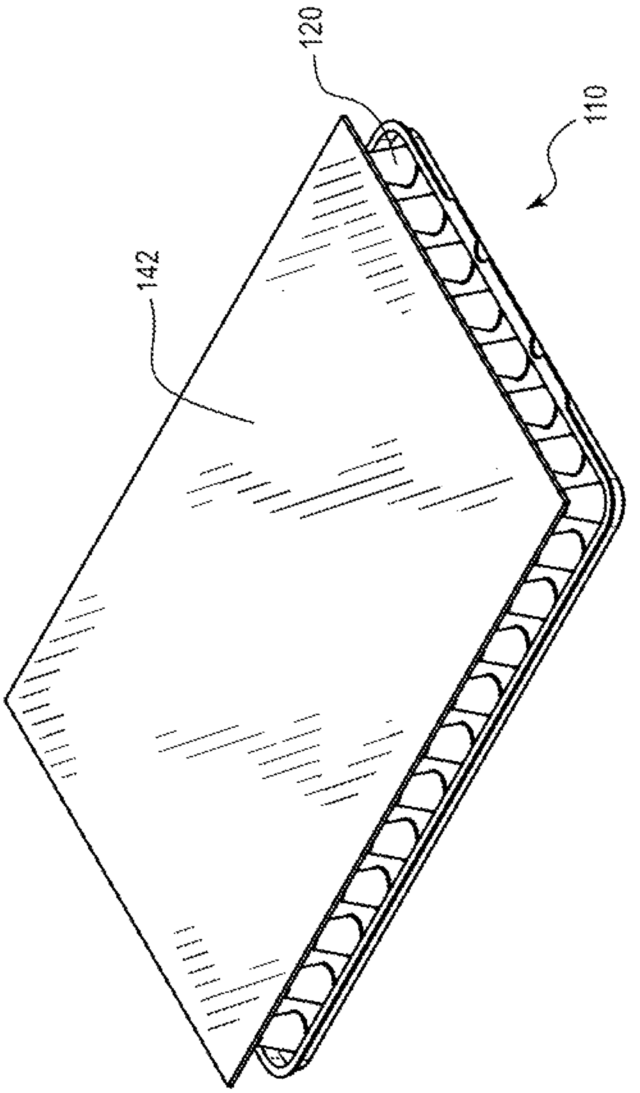
FIG. 15B is a perspective view of the well block and a base plate after they are joined together.
Figure 15C:
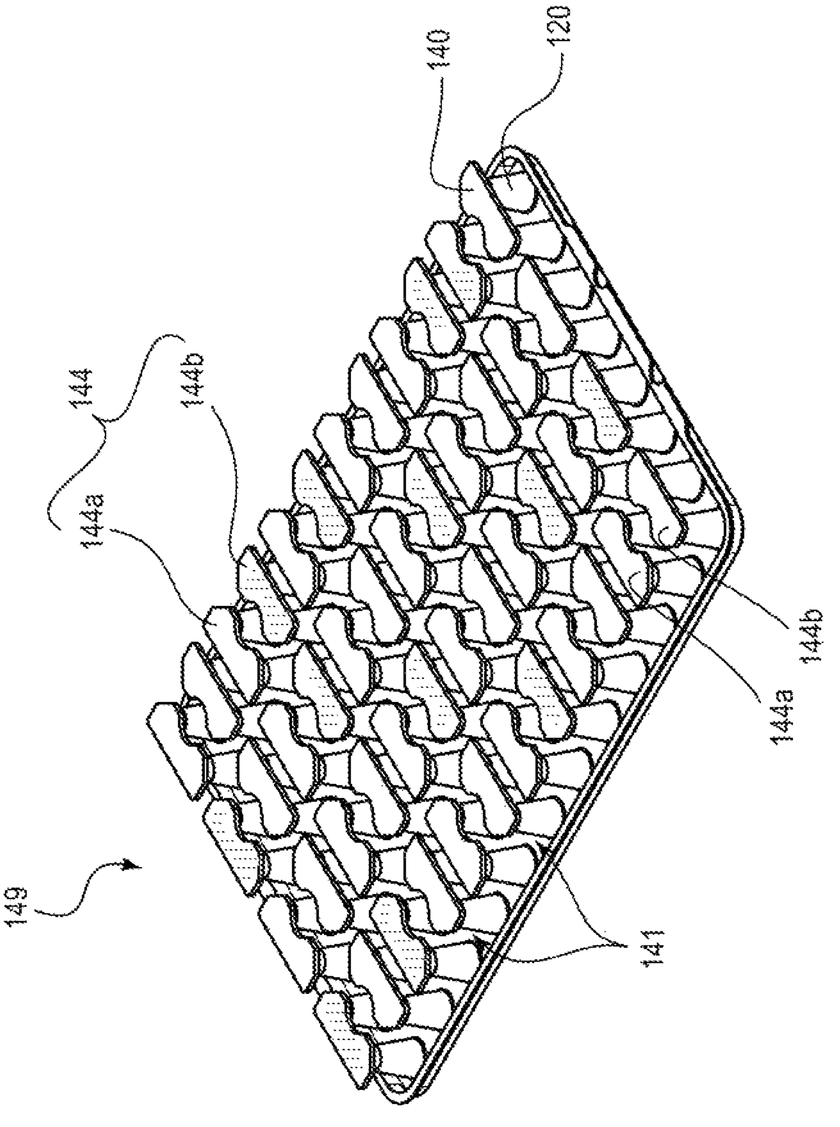
FIG. 15C is a perspective view, looking at the bottom of the wells, of the well block and paired sections of the base plate after removal of portions of the base plate.
Figure 16:
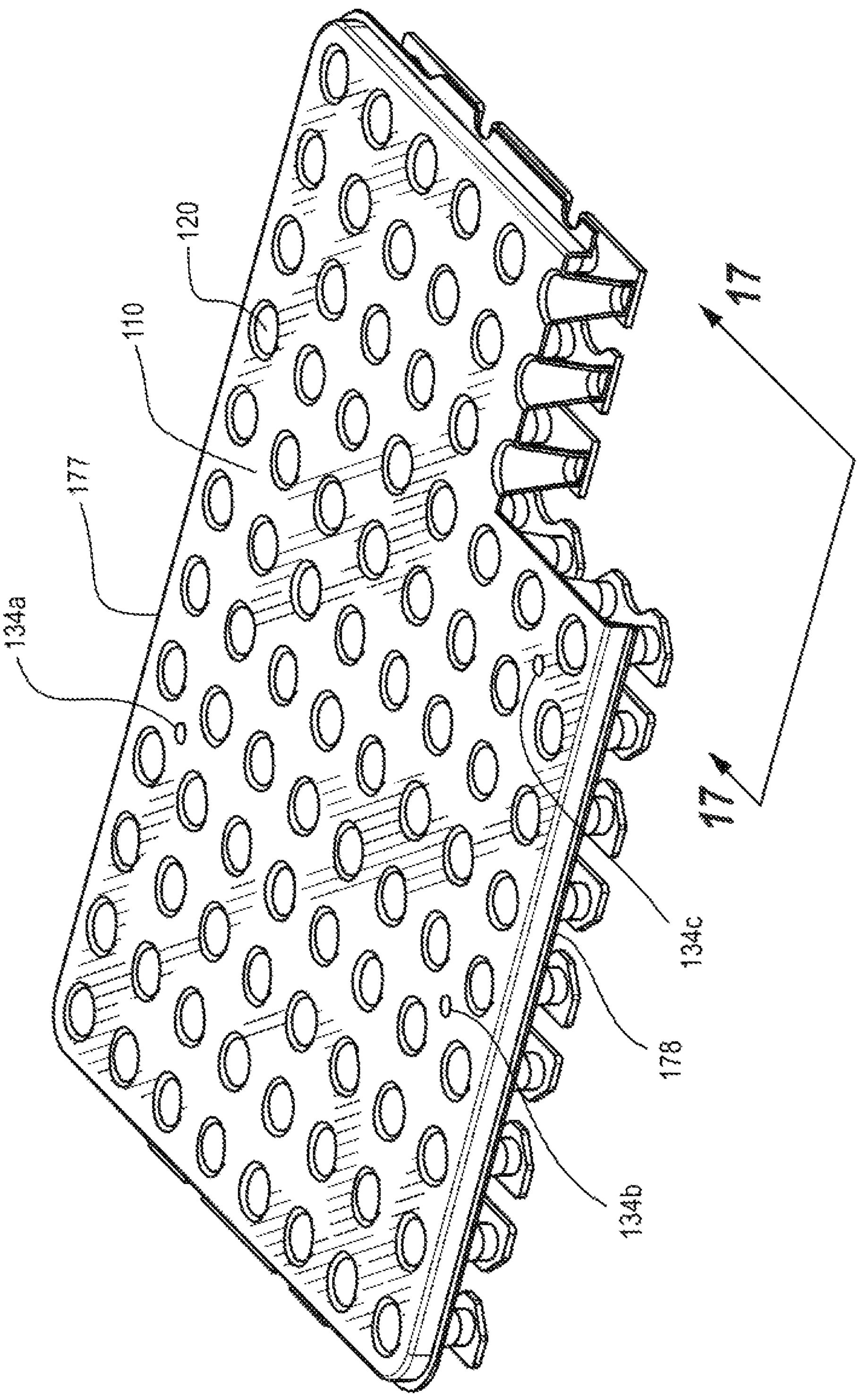
FIG. 16 is a perspective view, looking into the wells, of the well block and paired sections of the base plate after removal of portions of the base plate.
Figure 17:
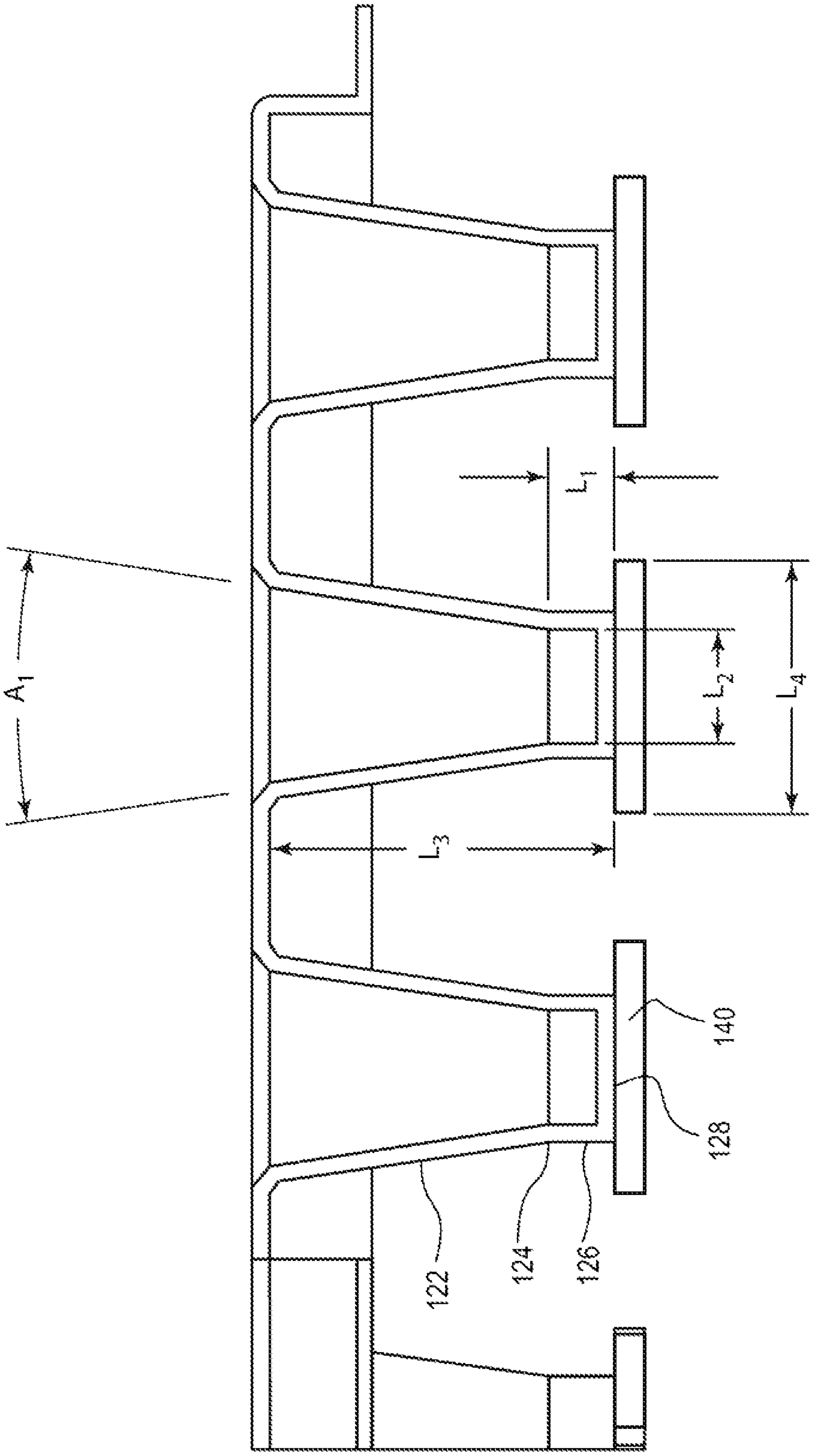
FIG. 17 is a side cross-sectional view, of the well block and paired sections of the base plate after removal of portions of the base plate.
Figure 26:
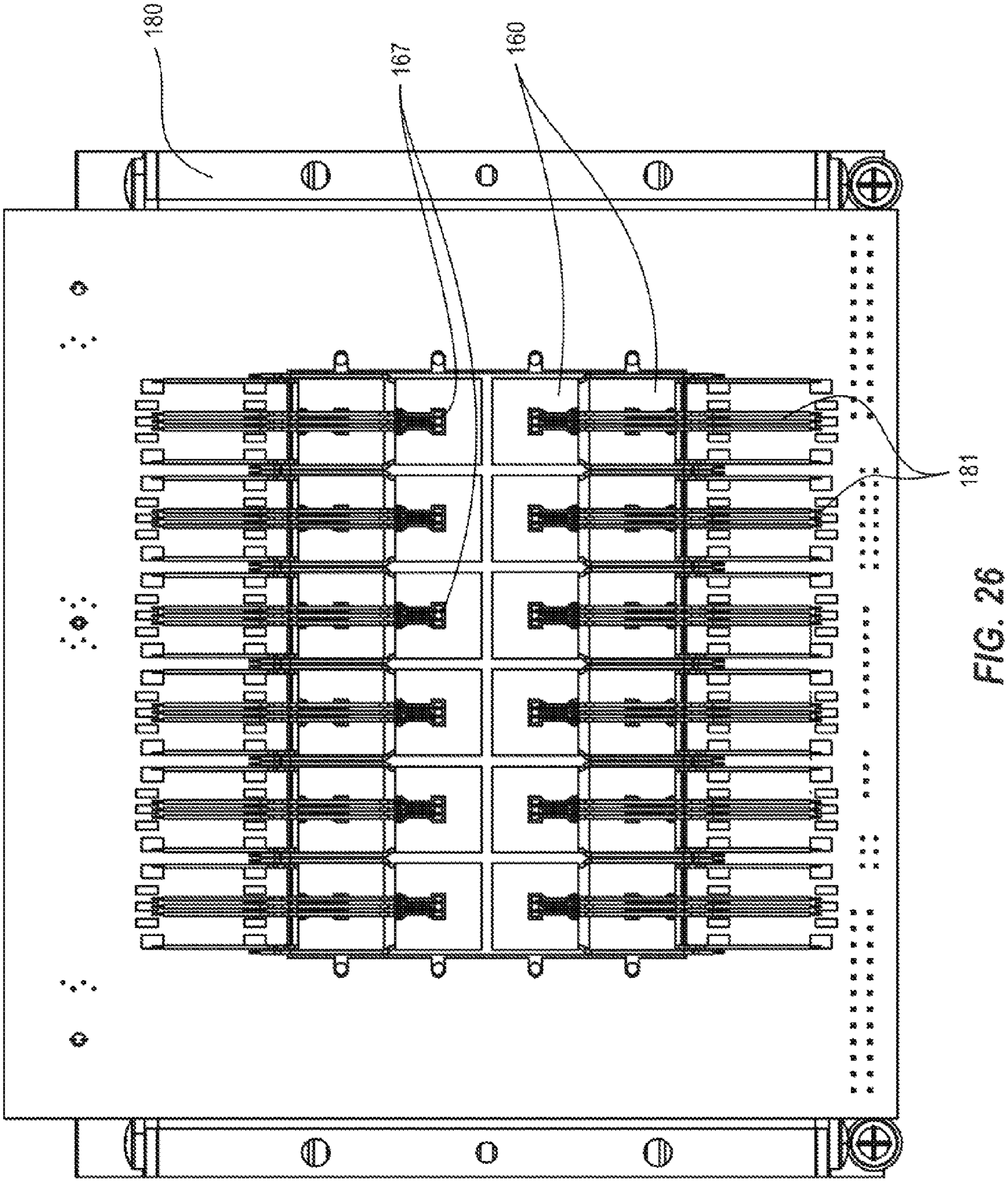
FIG. 26 is a perspective view of a series of twenty-four peltier devices on a printed circuit and the wires that connect the devices with the printed circuit.
Figure 27:
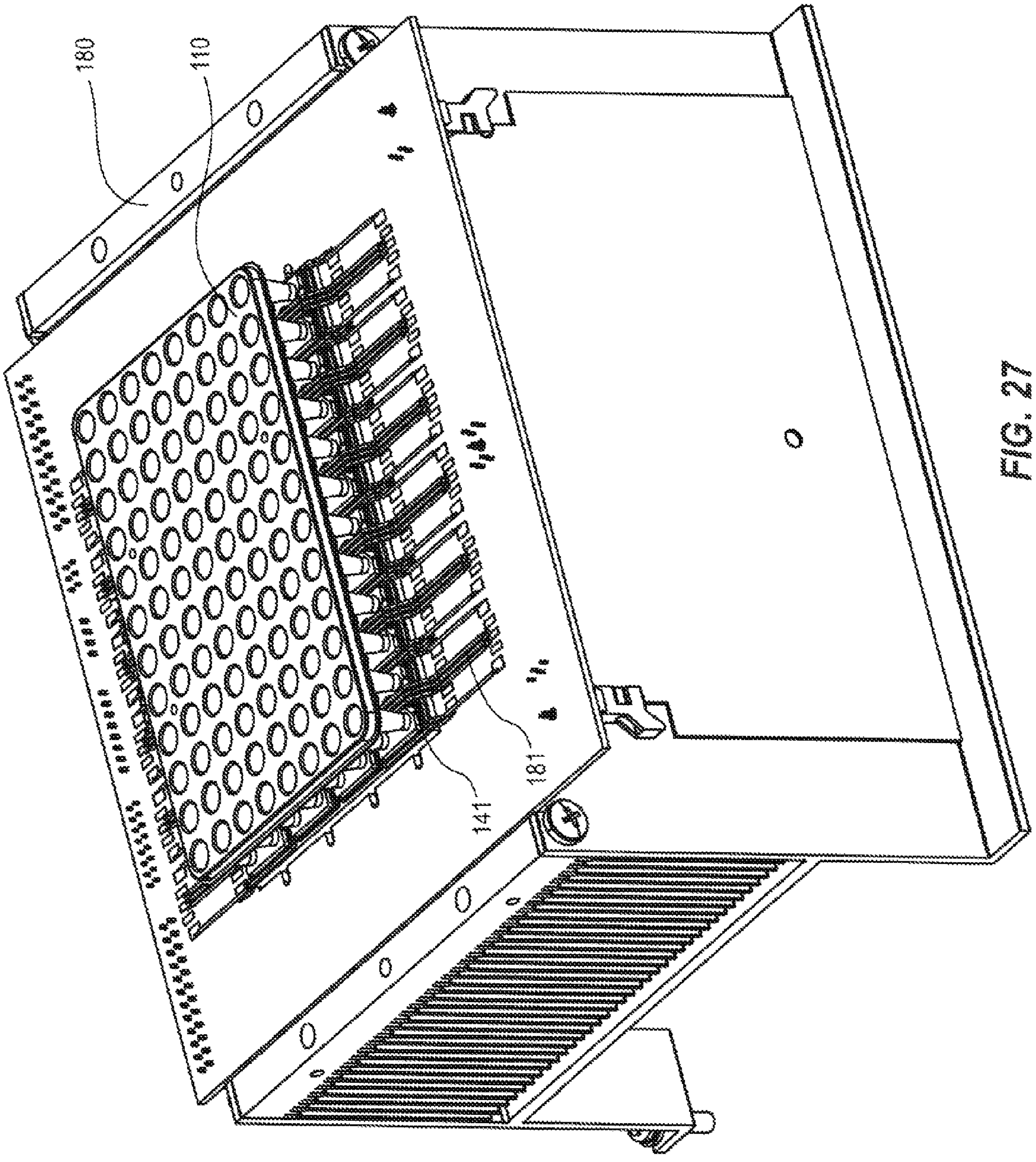
FIG. 27 is a perspective view of a well block on the peltier devices shown in FIG. 26 and their associated wires.

FIGS. 15A-15C depict an illustrative method of manufacturing a well block assembly 149 to yield pairs of base plates on the bottoms of wells. First a precursor base plate sheet 142 is obtained as shown in FIG. 15A and then is attached to flat bottom 128 illustratively by soldering, as illustrated in FIG. 15B. Then, portions of the precursor base plate sheet are removed to yield pairs of base plates **144*a*, 144*b* that span adjacent wells, as shown in FIG. 15C. The portions of the base plate sheet may be removed by any conventional method such as machining, punching, stamping, or dicing. Alternatively, the base sheet could be cut first and the base plates added thereto. By removing portions of precursor sheet 142, channels 141 are formed that may be used as space for wiring, illustratively to wire the peltiers 160 or temperature detectors 167, as shown in FIGS. 26-27. FIG. 16 shows another view of well block 110 with paired sections of the base plate. FIG. 17 provides the identification of the length of base plate 140**, which is $L_4$.

Figure 19:
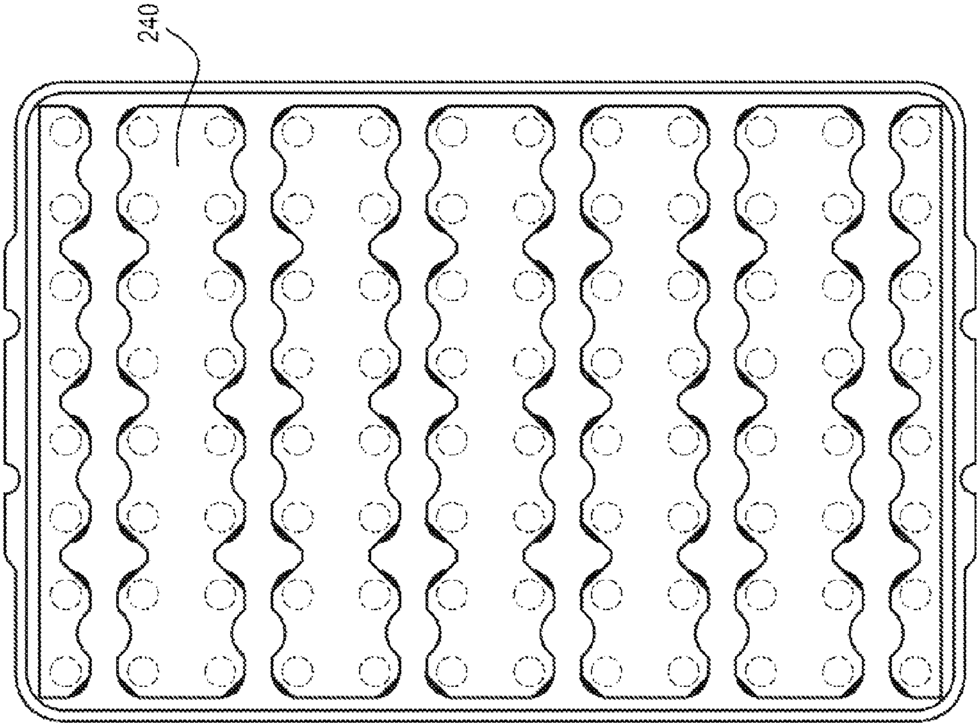
FIG. 19 is a plan view of sections of the base plate that are on a plurality of wells of a well block.
Figure 18:
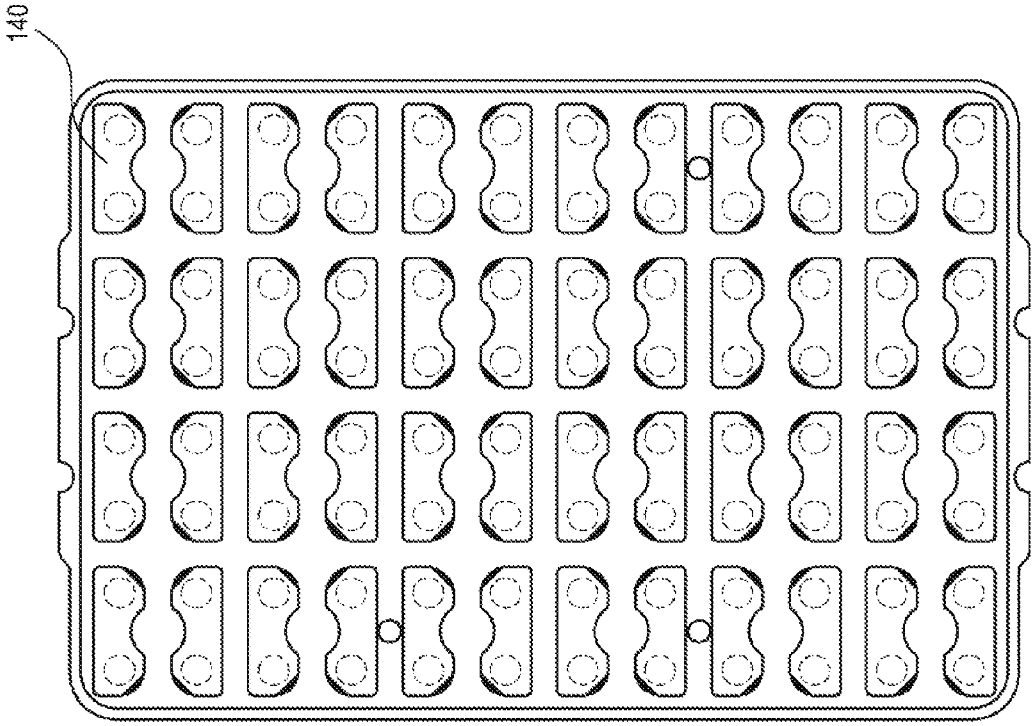
FIG. 18 is a plan view of the paired section of the base plate on the well block as shown in FIGS. 15C-17.

FIGS. 18 and 19 provide the same view of different embodiments. FIG. 18 corresponds with apparatus 100. FIG. 19 shows base plates 240 that connects more than four wells. Such an embodiment may result in increased uniformity, albeit with a reduction in control. Base plates 240 are also more easily used with a clamp bar such as clamp bar 230 shown in FIGS. 8A-8B and FIG. 11. A solid base plate may be acceptable in some embodiments, illustratively with recessed temperature sensors.

Figure 20:
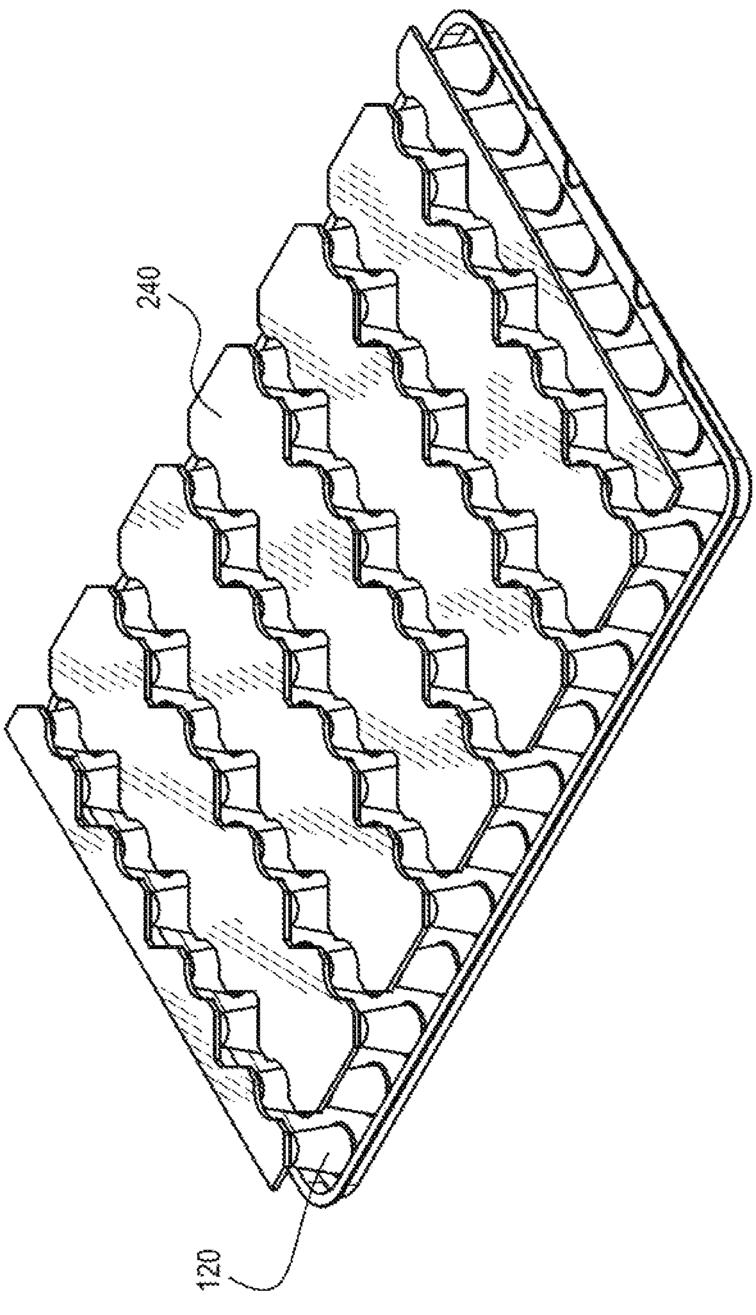
FIG. 20 is a perspective view of sections of the base plate that are on a plurality of wells of a well block.
Figure 21:
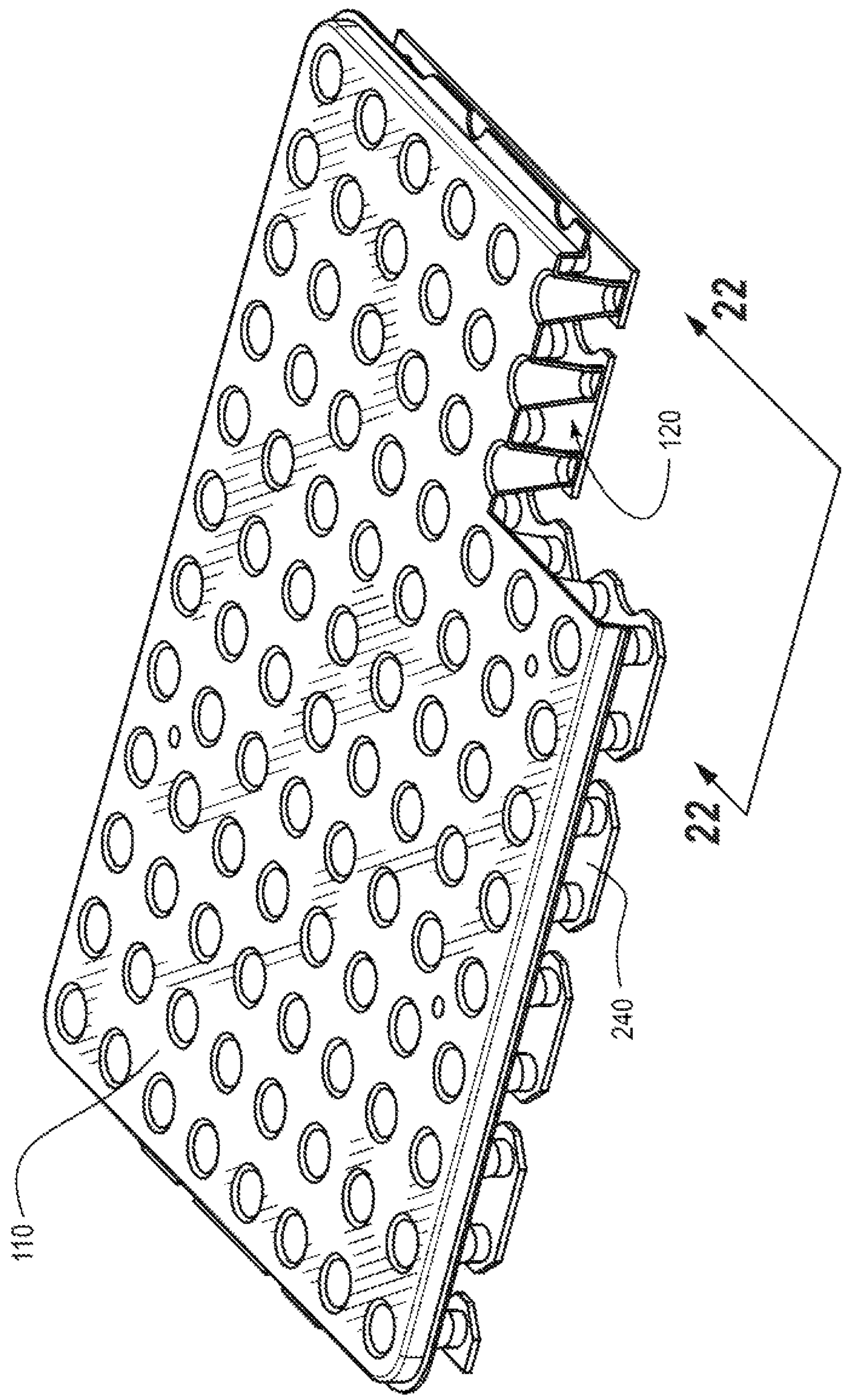
FIG. 21 is a perspective view, looking into the wells of the well block and sections of the base plate on a plurality of wells of the well block.
Figure 22:
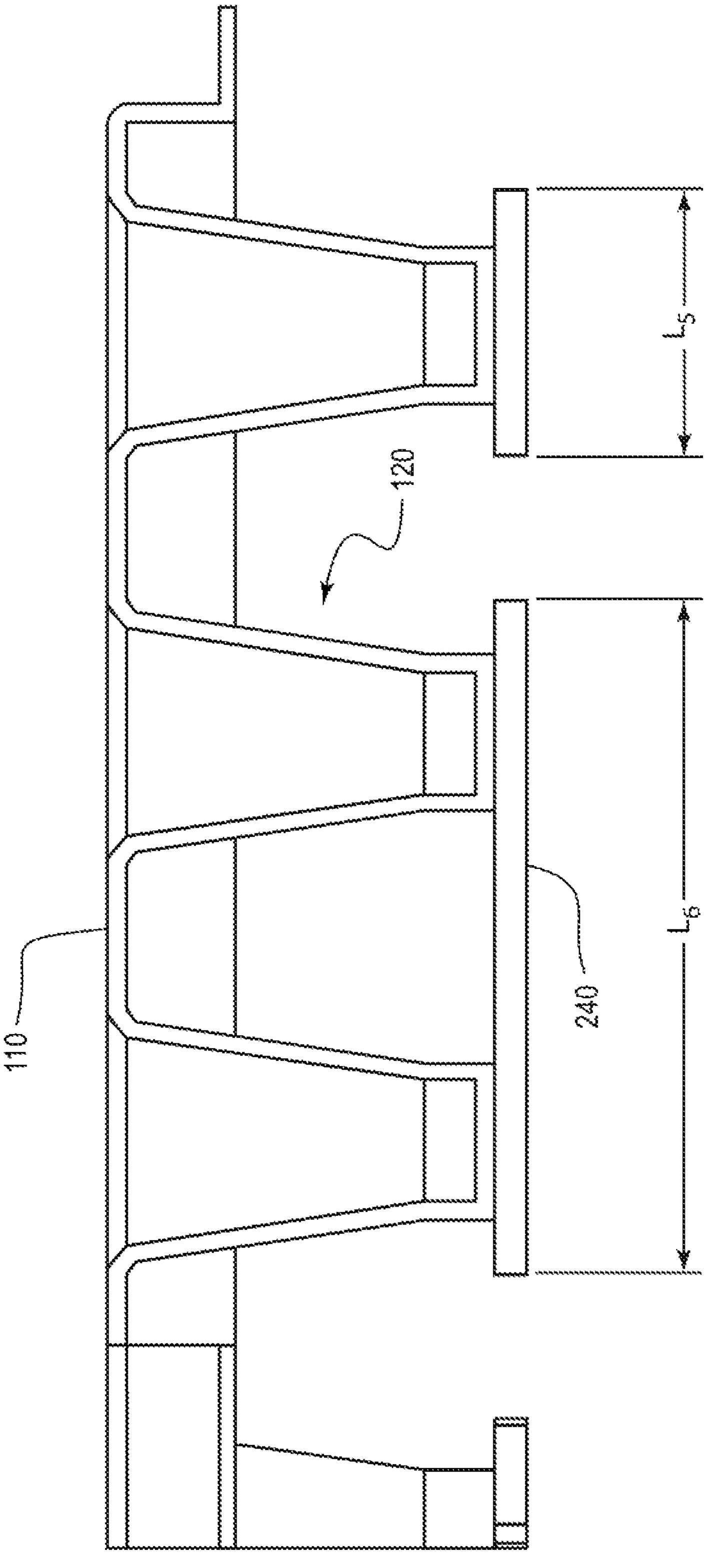
FIG. 22 is a side cross-sectional view, of the well block and sections of the base plate on a plurality of wells of a well block.

FIGS. 20-22 show the same embodiment depicted in FIG. 19 but from a different views. FIG. 22 provides the identification of the length of base plate 140', which is $L_5$ when it spans wells that are at the perimeter and is $L_6$ when it spans wells not at the perimeter.

Figure 23B:
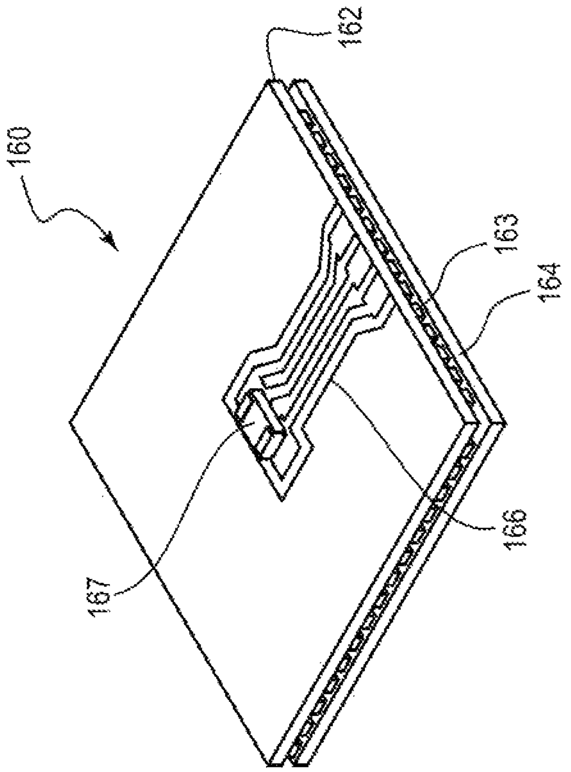
FIG. 23B is a perspective view of a temperature detector on a peltier device.
Figure 23A:
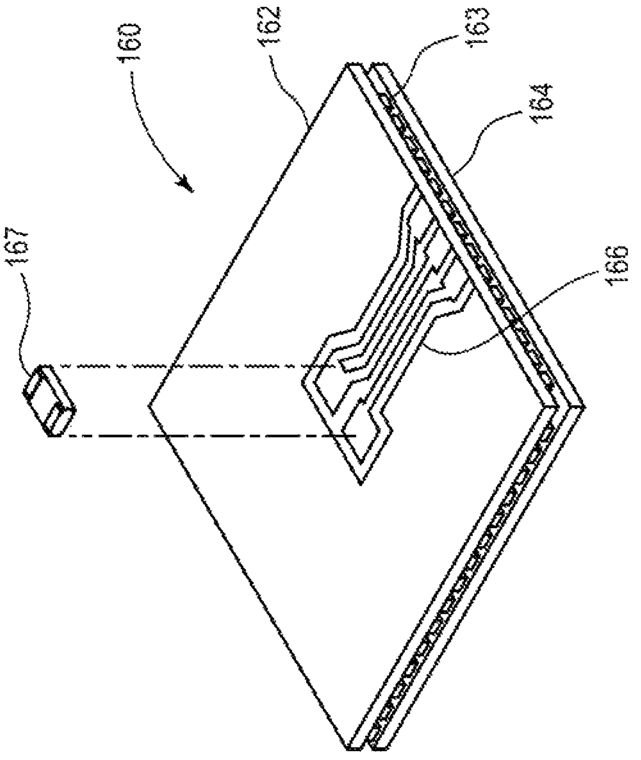
FIG. 23A is a perspective view of a peltier device receiving a temperature detector.

FIGS. 23A-23B provide more detailed views of peltier device 160. Between plates 162 and 164, heat directing element 163 is connected to printed circuit 166, which is connected, illustratively by solder or adhesive, to a temperature detector 167, illustratively a resistance temperature detector.

Figure 24:
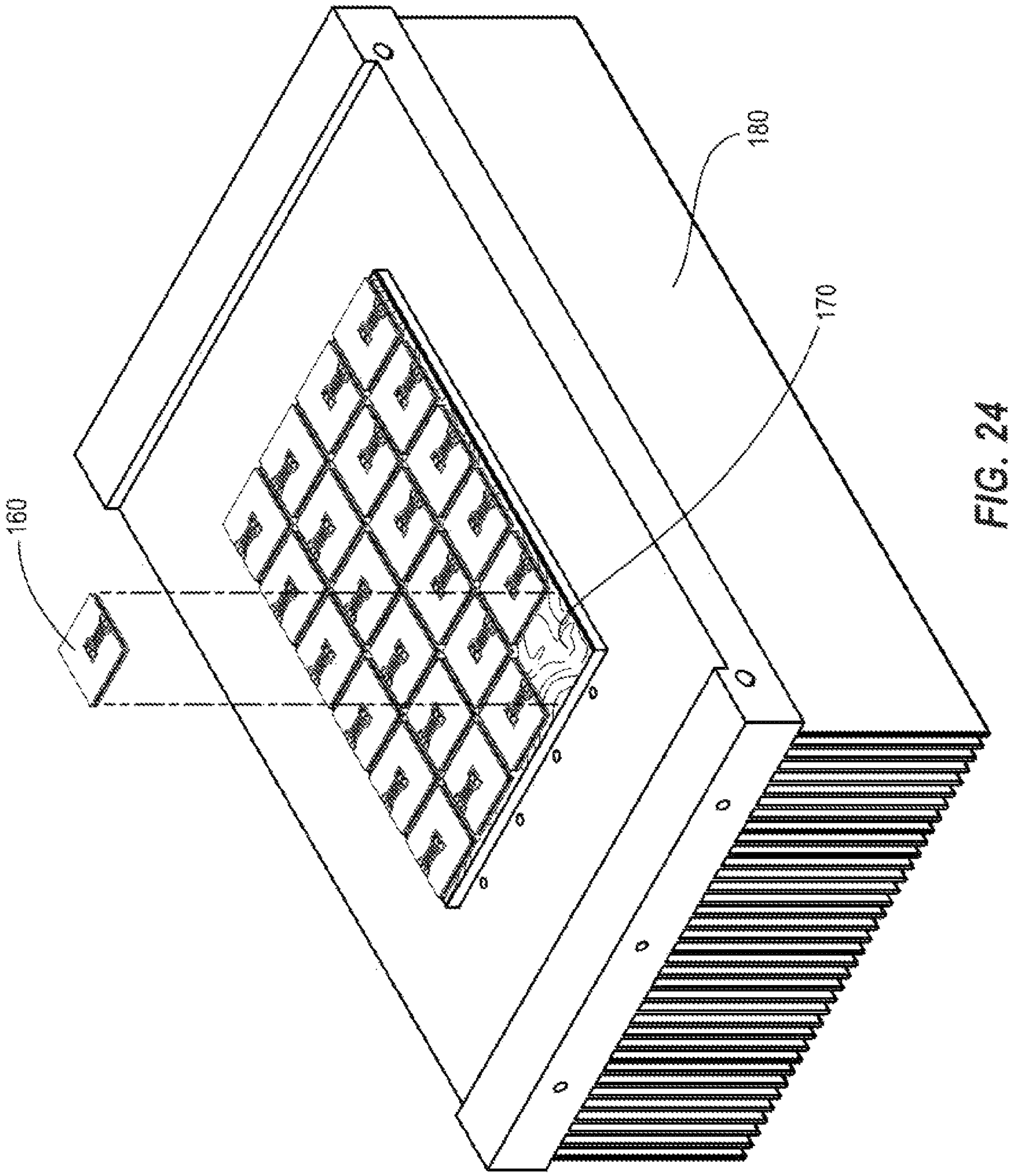
FIG. 24 is a perspective view of a peltier device on an adhesive on a heat sink.
Figure 25:
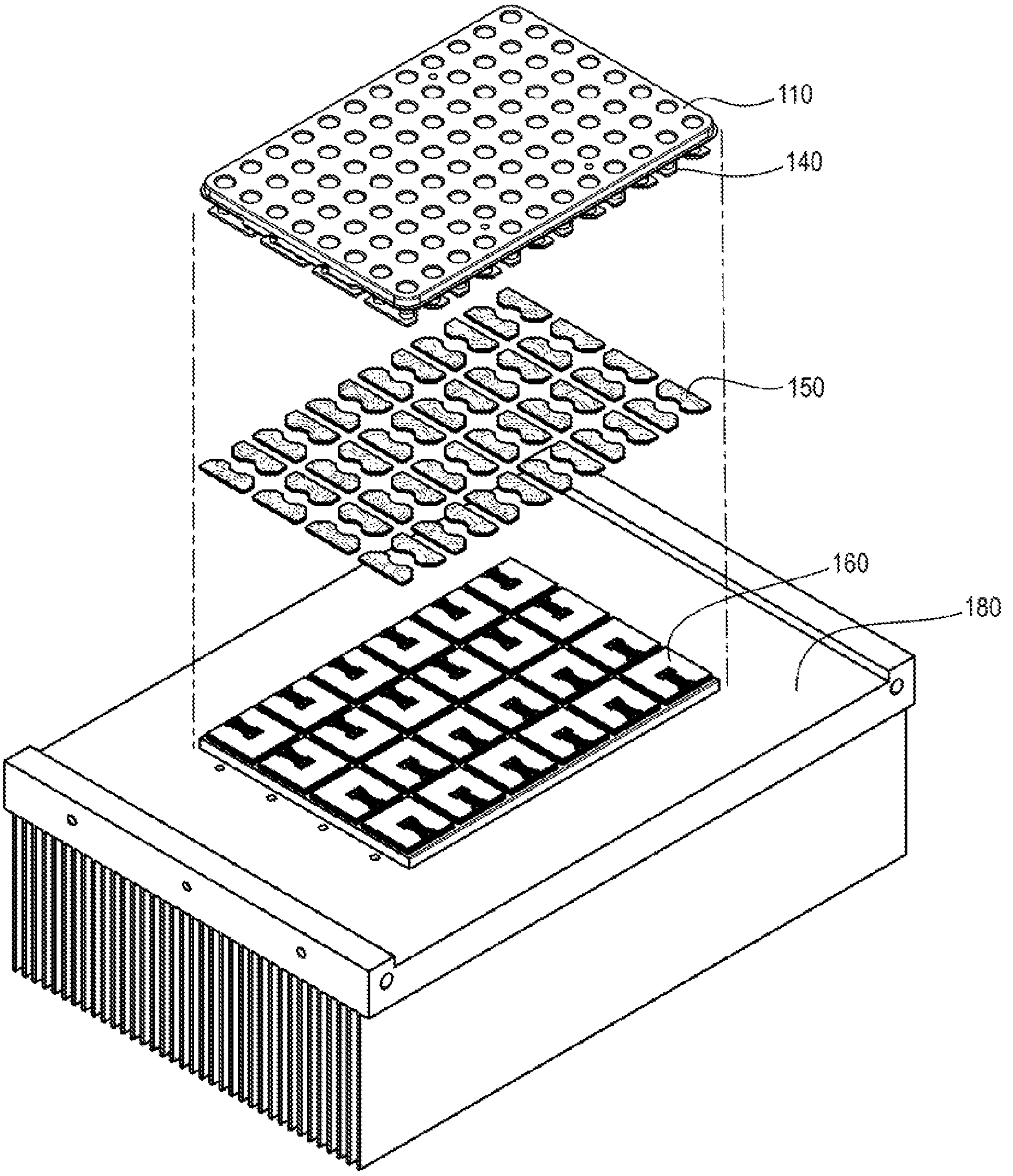
FIG. 25 is an exploded perspective view of peltier devices on a well block, adhesive, and base plates attached to a well block.

FIGS. 24-25 depict a method of manufacturing apparatus 100. FIG. 24 shows peltier device 160 being placed on adhesive 170. FIG. 25 shows the subsequent steps of placing adhesive 150 on peltiers 160 followed by placement of base plates 140 on adhesive 150. An advantage of this configuration is that clamps or screws such as those described above are not necessary. However, use of such clamps or screws is not precluded with apparatus 100.

As shown in FIGS. 24-25 twenty-four peltiers 160 are used, although it is understood that more or fewer peltiers 160 may be used, depending on the desired application. Illustratively, for a 96-well plate, between 4 and 96 peltiers may be used, with zones of 24 wells if 4 peltiers are used, down to zones of one well, with each peltier controlling an individual well. In one illustrative embodiment, each peltier device 160 is individually driven. Illustratively, the peltiers 160 are not in series nor parallel. Such may be used to provide greater well-to-well uniformity, for example by heating the exterior peltiers to a slightly higher temperature, thus reducing the issue of cooler maximum temperatures in the exterior wells, particularly in the corner wells. Individually driven peltiers 160 also may be used to provide for a temperature gradient across the plate.

FIG. 26 is a perspective view of a series of twenty-four peltier devices 160 on heat sink 180 and their wires that connect peltier devices 160 to a printed circuit. The printed circuit is connected to the temperature detectors 167.

FIG. 27 shows well block 110 on peltier devices shown in FIG. 26 and their associated wires 181. As seen in FIG. 15C, there is a channel 141, which is a space, between each pair of base plates 140, so when well block 110 and base plates 140 are placed on peltier devices 160, the wires extending from peltier devices 160 may extend through this space.

Figure 28:
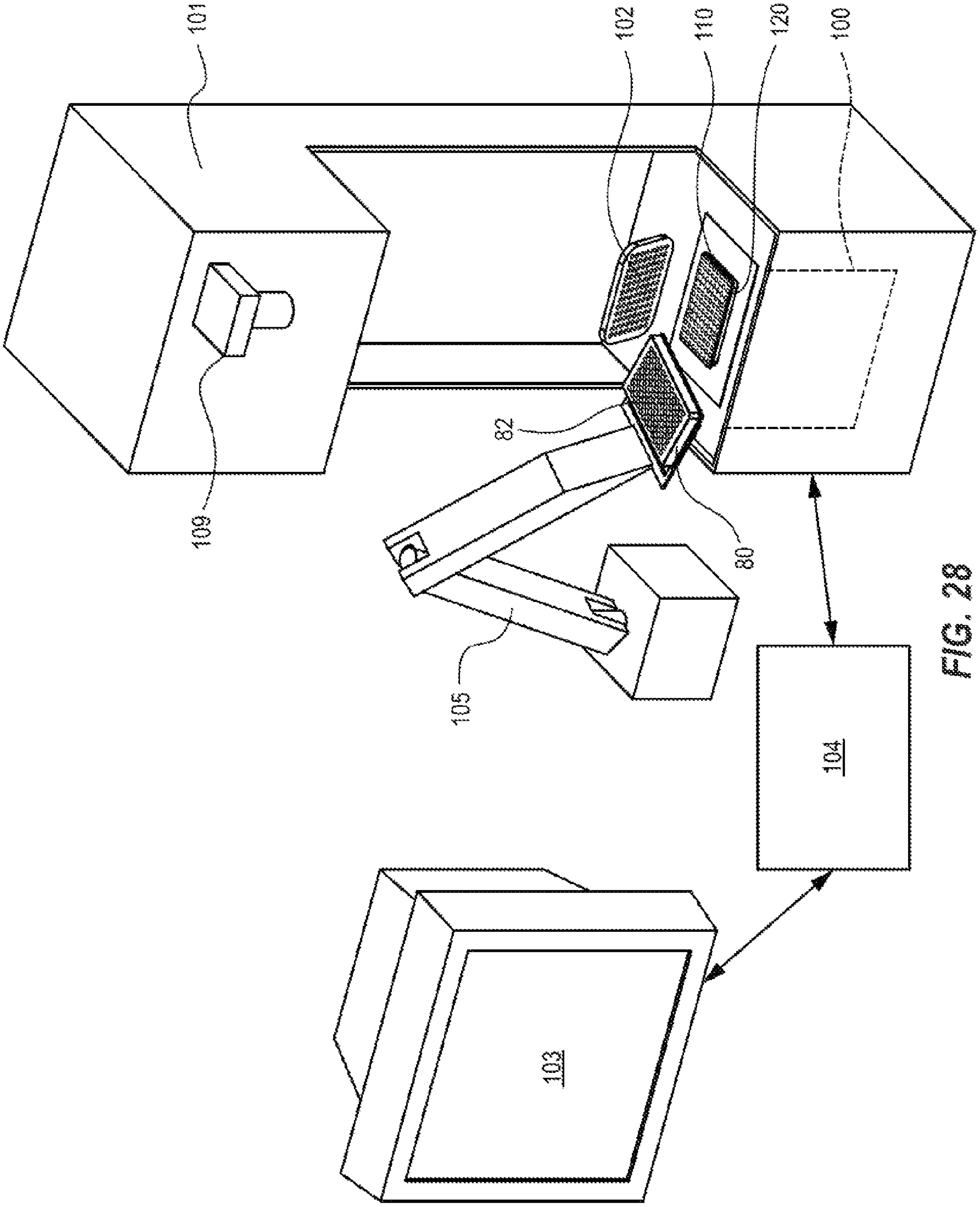
FIG. 28 is a block diagram of an automated system for nucleic acid amplification and analysis.

FIG. 28 shows an automated system containing thermal cycler apparatus 100. Thermal cycler apparatus 100, is mounted within a housing 101. Well block 110 is positioned to receive sample plate 80 once sample plate 80 is inserted into opening 102. Opening 102, as shown in FIG. 28 is a movable lid, but it is understood that opening 102 can be any type of opening as are known in the art, including a slot, a door, etc. Optionally, the lid mechanism may close down onto sample plate 80 to seal the sample within sample wells 82 or to force wells 82 of sample plate 80 into better contact with wells 120 of well block 110. If real-time data acquisition or post-PCR melting is desired, an optics block 109 may be provided for sample excitation and detection. Optics block 109 may provide single-color or multi-color detection, as is known in the art.

The system includes a computing device 104, which may comprise one or more processors, memories, computer-readable media, one or more HMI devices 103 (e.g., input-output devices, displays, printers, and the like), one or more communications interfaces (e.g., network interfaces, Universal Serial Bus (USB) interfaces, etc.), and the like. Computing device 104 may be provided within housing 101, or may be provided separately, such as a laptop or desktop computer, or portions of computing device 104 may be resident within housing 101, while other portions are located separately and may be coupled through wiring or wirelessly. Computing device 104 may be configured to load computer-readable program code for controlling thermal cycler apparatus 100 and optics block 109. In one illustrative embodiment, thermal cycler apparatus 100 in housing 101 may be provided in an automated system with a robotics unit 105. The robotics unit 105 may be programmed to load the samples into sample wells 82 and then load sample plate 80 into housing 101 through opening 102. Optionally, robotics unit 105 may also prepare the samples prior to loading into sample wells 82. Teach points may be used by robotics unit 105 for orienting plate 80 into well block 110. Teach points 134*a-c* are best seen in FIG. 16, where three teach points are used. In this illustrative arrangement, teach point 134*a* is located near a first edge 177, while teach points 134*b* and 134*c* are located near a second edge 178 of well block 110. With three teach points, the robotics unit 105 can easily identify the orientation of well block 110. However, it is understood that three teach points is illustrative and any number of teach points can be used. Control of robotics unit 105 may be through computing device 104, or robotics unit 105 may be controlled by a separate processor. Optionally, robotics unit 105 may be configured to load samples into multiple thermal cycler devices.

Examples of an Adhesive.

An exemplary method for determining the tensile strength and elongation of elastomeric materials is described below. This method is not ASTM D412 but is based closely thereon. For this exemplary method, the apparatus may be the following, although similar equipment may be used provided it is capable of the accuracy and precision required. The dies used may be the ASTM D412 die C or others as specified, from any suitable source. The marker used may be a bench marker with two parallel lines 1+/−0.003 in. (2.54+/−0.0076 cm) apart for dies C and D and 2+/−0.003 in. (5.08/+/−0.0076 cm) for A, B, E and F, from any suitable source of commercial rubber stamp pads. The micrometer used should be capable to +/−0.001 in. (0.02 mm) and exert a total force of no more than 1.5 psi (10 kpa), from any suitable source. The molds used may be aluminum and may prepare samples at least 4 in.×4 in. (10.2 cm×10.2 cm) and between 0.06 in and 0.12 in. (0.15 cm and 0.30 cm) thick, as specified, from any suitable source. The press may be any small hand operated press suitable for cutting the test bars. Examples of such presses include tensile testers from Monsanto Instruments, Akron, Ohio; Instron Corp., Canton, Mass.; or United Testing Systems, Auburn Heights, Mich.

It is noted, and a skilled artisan would be aware, that the results may be adversely affected by improper care of the dies. The edges should be sharp and protected at all times from nicks.

A standard test slab (0.080+/−0.008 inches thick, 2.0+/−0.2 mm) of the material to be tested was molded and cured as specified. The slab was allowed to rest at room temperature on a flat surface for at least 3 h. The room in which the testing was performed was maintained at 23+/−2° C. Using the ASTM D412 Disc or other specified die and a press, three bars (or the specified number of test bars) were cut parallel with the grain, if any, of the material.

It is noted that straight samples may be pulled if enough material is not available to cut the normal test bars; however, the width must be measured. In these instances, A=W/[(D)(L)] where A is the area in $cm^2$; W is the weight in air in g; D is the density in $g/cm^3$; and L is the length in cm. Similarly, pieces of tubing too small to cut suitable bars from may be pulled, if the area is calculated. For tubing with OD ⅜ in. (0.95 cm) or less, this may be approximated. In other instances, A=(CSA,1)−(CSA,2); where CSA,1 is the area using outside diameter and CSA,2 is the area using inside diameter.

The thickness {to 0.001 in. (0.02 mm)} of each test bar was measured in three places from end to end of the reduced section. The median of the three measurements was recorded as "Th". If the measurements varied by more than 0.003 in. (0.07 mm), the bar was discarded. For instances where tension set is required, each of the test bars was marked with a 1 in. (2.54 cm), "L,o" bench mark that was equidistant from the center line of the reduced section and perpendicular to its longitudinal axis. It is noted that whenever samples were heat aged or stored prior to testing, they are marked for identification by notching the ends rather than with an ink mark if there is the possibility of the ink affecting the samples.

The test bar was placed in the grips of the tester and adjusted so the tension was uniformly distributed over the cross section of the bar during the test. The machine was started, the bar was stretched to the breaking point and the necessary data to complete the calculations as specified was recorded. It is noted that the instrument may be equipped with a mechanical or electrical measuring system and may have a manual or automatic recording system. The calculations may be performed by a computer attached to the test instrument.

In this exemplary method, the rupture points of the bars should be observed as an indication of problem with the dies. Thus, if all samples break in the same area, a die problem may exist. If this occurred, the test was repeated with the remaining test bars. The required result was calculated and the median values were reported unless another reporting mode is specified. If specified, other reporting modes or values may be reported, e.g. average, weighted average, lowest value, highest value.

The median value of three bars was used unless either one or more of the values did not meet the specified requirements when testing for compliance with a specification, or the sample was a referee or round robin material. In these instances, a total of five bars were pulled and the median value reported.

If there was any indication that the results were invalid, the total test was repeated. Examples of such indications are minimum and maximum values+/−15% from the median; constant rupture point on all bars (i.e. a damaged die); nicks in the edges of the bars due to poor cutting techniques or damaged dies; and air bubbles, flow marks, etc., which might indicate poor sample preparation.

If tension set is required, the two pieces were allowed to rest 10 min, then carefully fit together to give full contact at the point of the break. The distance between the bench marks was measured and recorded as "L,2".

In this exemplary method, the tensile tester, bench marker, and micrometer were on a routine calibration schedule.

The following definitions are applied to terms used in this method.

Elongation is the extension of a test bar to rupture expressed as a percentage of the original length and measured by the bench marks. It is also known as ultimate elongation or elongation at break. The term may also be used to describe a specific percentage extension when used with modulus or tension set (i.e. modulus at 200% elongation). Elongation, 5 is calculated as [{(L,1)−(L,o)} (100)]/(L,o) where L,1 is the length at break between bench marks and I,o is the original length between bench marks. With an elongation gage and a 1 in. (2.54 cm) bench mark spacing, the percentage elongation may be read directly as E, %.

Modulus is the applied force per unit of original cross sectional area of a test bar at a specific percentage elongation (i.e. tensile stress at a given elongation). This term is normally accompanied with a specified percentage elongation and is generally written "Modulus, 200." Modulus is calculated as [(F) (Factor)]/[(W) (Th)]=psi #, where F is the force applied or the dial reading at E; Factor is instrumental factors required to convert the dial reading into pounds of force; W is width of the reduced section before pulling {0.250 in. (0.635 cm) for die C}; "Th" median thickness of the reduced section before pulling, E is specified percentage elongation, and # KPa is psi×6.8948.

Tensile strength is the maximum tensile stress applied during the rupture of a test bar. Tensile strength is calculated as [(F) (Factor)]/[(W) (Th)]=psi #, where all symbols are as defined as above except F; F is the maximum force applied to break the sample.

Tensile stress is the applied force per unit of original cross sectional area of a test bar.

Tension set after break is the set (extension) remaining after a test bar has been stretched to rupture and allowed to retract for 10 min, expressed as a percentage of the original length of the bench mark. This is not to be confused with tension set. Tension set after break is calculated as Set, %=[{(L,2)=(L,o)} (100)]/(L,o), where L,o is the original length between bench mark and L,2 is the length between bench marks after 10 min rest after break.

Tension set is the set (extension) remaining after a test bar has been stretched to a given percentage elongation and allowed to retract, expressed as a percentage of the original length of the bench mark. The value is obtained as follows: the bar is placed in the grips. The grips are spread at 20 in./min (50.8+/−2.5 cm/min) to the specified percentage elongation. The machine is secured and the sample is allowed to remain under tension for a specified time. The sample is released quickly but without snap and the bar is removed. The bar is allowed to rest flat for a specified time and the distance between the bench marks to 1% of the original length is measured. Calculate as for tension set after break. The result is generally reported with the percentage elongation, such as "tension set, 200."

The precision of the various results should be within +/−15% to ensure repeatability, reproducibility, and accuracy.

The thermally conductive compounds listed in Table 1, below, are available from DOW CORNING, and were all tested using the exemplary method described previously. Relevant data is shown.

TABLE 1

Thermal conductivity at 25° C./77° F., Watt/meter-K; Elongation, %; Viscosity, centipoise; and Unprimed Adhesion Lap Shear, kgf/$cm^2$.

| product | thermal conductivity | elongation | viscosity | unprimed adhesion lap shear |
|---|---|---|---|---|
| SE4420 | 0.9 | 90 | 108,000 | 35 |
| SE4422 | 0.9 | 120 | 200,000 | 16 |
| SE4486 | 1.53 | 50 | 19,000 | 14 |
| SE9184 | 0.84 | 70 | nonflow | 21 |
| SE4400 | 0.92 | 90 | 76,000 | 30.9 |
| SE4402 | 0.92 | 120 | 34,000 | 34 |
| SE4450 | 1.97 | 40 | 61,000 | 37 |
| 1-4173 | 1.9 | 20 | 58,000 | 45 |
| 1-4174 | 1.9 | 22 | 58,000 | 41 |
| Q1-9226 | 0.74 | 110 | 50,000 | NA |
| 3-1818 | 1.8 | 20 | 68,700 | 35.9 |
| Q3-3600 | 0.77 | 55 | 4,700 | NA |
| 3-6605 | 0.85 | 90 | 47,000 | 24.6 |
| 3-6751 | 1.1 | 35 | 10,000 | 39 |
| 3-6752 | 1.8 | 15 | 81,000 | 37.9 |
| 3-6753 | 1.4 | 35 | 11,000 | 37.9 |
| SE4410 | 0.92 | 60 | 3,500 | 26 |
| SE4447 | 2.5 | 20 | 140,000 | NA |
| SE4448 | 2.2 | NA | 102,000 | NA |
| 3-6651 | 1.1 | 180 | 32,000 | NA |
| 3-6652 | 1.9 | 70 | 34,000 | NA |
| 3-6655 | 1.8 | 90 | 33,000 | NA |

The compound AS 1808, available from ACC SILICONES (Somerset, UK), was tested using a method comparable to the exemplary method described previously. Its thermal conductivity at 25° C./77° F. (Watt/meter-K), Elongation (%), and Overlap Shear Strength Aluminum (kg/cm2) are 1.79, 91, and 12.31, respectively.

It will be understood that reference to PCR is illustrative only and the devices of this disclosure may be compatible with other methods of amplification. Such suitable procedures include strand displacement amplification (SDA); nucleic acid sequence-based amplification (NASBA); cascade rolling circle amplification (CRCA), Q beta replicase mediated amplification; isothermal and chimeric primer-initiated amplification of nucleic acids (ICAN); transcription-mediated amplification (TMA), and the like. Asymmetric PCR may also be used. Therefore, when the term PCR is used herein, it should be understood to include variations on PCR as well as other alternative amplification methods, as well as post-PCR processing, such as melt curve analysis. Illustrative examples of suitable melt curve analysis can be found in U.S. Pat. No. 7,387,887, which is incorporated herein by reference. Furthermore, the devices of this disclosure may be suitable for a variety of other biological and non-biological reactions that require temperature control.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

The claims following this Detailed Description are hereby expressly incorporated into this Detailed Description, with each claim standing on its own as a separate embodiment. This disclosure includes all permutations of the independent claims with their dependent claims. Recitation in the claims of the term "first" with respect to a feature or element does not necessarily imply the existence of a second or additional such feature or element. Embodiments of the invention in which an exclusive property or privilege is claimed are defined as follows.

The invention claimed is:

1. A thermal cycler apparatus, comprising:

a peltier device;

an elastomeric adhesive on the peltier device, wherein the elastomeric adhesive is a thermally conductive, non-curing silicone;

a well block coupled to the peltier device; and a heat sink coupled to the peltier device;

wherein the well block and the heat sink are coupled to the peltier device via the elastomeric adhesive and the well block is not clamped to the heat sink, and the elastomeric adhesive has an elastomeric property between about 15% and about 1,000%, the elastomeric adhesive has a further elastomeric property of remaining ductile and flexible even after at least about 5,000 temperature cycles between a temperature at least as high as 95° C. and at least as low as 60° C. such that the elastomeric adhesive can still couple the well block and the heat sink to the peltier device;

the elastomeric adhesive has a thermal conductivity at 25° C./77° F. of between about 0.7 Watt/meter-K and about 2.5 Watt/meter-K.

2. The thermal cycler apparatus of claim 1, wherein the adhesive is located between the well block and the peltier plate.

3. The thermal cycler apparatus of claim 1, wherein the adhesive is located between the peltier plate and the heat sink.

4. The thermal cycler apparatus of claim 1, wherein the adhesive is located between the well block and the peltier, and wherein the adhesive is also located between the peltier and the heat sink.

5. The thermal cycler apparatus of claim 1, wherein the peltier device is coupled to the heat sink by the adhesive.

6. The thermal cycler apparatus of claim 1, wherein the well block comprises a plurality of wells, wherein each well comprises a generally cylindrical portion located below a conical portion and a flat bottom portion, and wherein the flat bottom portion is perpendicular to the generally cylindrical portion.

7. The thermal cycler apparatus of claim 1, wherein the elastomeric adhesive retains the peltier device adjacent to at least one of the well block and the heat sink when the apparatus is turned upside down.

8. The thermal cycler apparatus of claim 1, wherein the further elastomeric property of remaining ductile and flexible of the elastomeric adhesive remains even after cycling between a temperature at least as high as 95° C. and at least as low as 60° C. at least about 200,000.

9. The thermal cycler apparatus of claim 1, wherein the elastomeric adhesive has an elastomeric property of between about 35% and about 700% elongation.

10. The thermal cycler apparatus of claim 1, wherein the elastomeric adhesive has an unprimed adhesion lap shear of between about 1 $kgf/cm^2$ and about 75 $kgf/cm^2$.

11. The thermal cycler apparatus of claim 1, wherein the elastomeric adhesive has a viscosity of between about 1,000 centipoise and about 200,000 centipoise.

12. The thermal cycler apparatus of claim 1, wherein the elastomeric adhesive has a thermal conductivity at 25° C./77° F. of between about 0.8 Watt/meter-K and about 2 Watt/meter-K.

13. The thermal cycler apparatus of claim 1, wherein thermal cycler apparatus is provided in a housing, the housing further provided with an optics system.

14. The thermal cycler apparatus of claim 1, wherein the thermal cycler apparatus is provided with a computing device for controlling the thermal cycler apparatus.

15. The thermal cycler apparatus of claim 1, further provided with a robotics unit configured for loading samples into the thermal cycler apparatus.

16. The thermal cycler apparatus of claim 1, wherein, the well block comprises a plurality of wells, wherein each well comprises a generally cylindrical portion located below a conical portion and a flat bottom portion, wherein the flat bottom portion is perpendicular to the cylindrical portion, and wherein each individual well in the well block is configured to receive a sample well therein, wherein the sample well extends through the conical portion and into the cylindrical portion of the well;

a peltier device coupled to the well block; and, a heat sink coupled to the peltier device.

17. The thermal cycler apparatus of claim 16, wherein the conical portion forms an angle of about 16° with the cylindrical portion.

18. The thermal cycler apparatus of claim 16, wherein a wall of the generally cylindrical portion forms an angle with the flat bottom portion, the angle being between 90° and 95°.

19. The thermal cycler apparatus of claim 16, wherein the flat bottom portion contacts the peltier device.

20. The thermal cycler apparatus of claim 16, wherein the wells are each configured such that a conical sample well placed in each well cannot contact the flat bottom portion of the well.

21. The thermal cycler apparatus of claim 16, wherein the wells are each configured such when a conical sample well, comprising a conical portion, is placed in each well, the conical portion of the sample well contacts the conical portion of the well.

22. The thermal cycler apparatus of claim 16, wherein each flat bottom portion is coupled to a base plate.

23. The thermal cycler apparatus of claim 16, further comprising a plurality of peltier devices, wherein a predetermined number of wells are coupled to each peltier device to form a predetermined number of thermal zones in the well block.

24. The thermal cycler apparatus of claim 16, further comprising a first base plate coupled to a first pair of wells that are adjacent to each other, via the flat bottom portions of the wells, such that heat transferred to the first base plate is then transferred to the first pair of wells.

25. The thermal cycler apparatus of claim 24, further comprising a second base plate coupled to a second pair of wells that are adjacent to each other, via the flat bottom portions of the wells, wherein the first and second base plates are paired on the peltier device such that heat is transferred from the peltier device via the first and second base plates to a set of four wells comprising the first and second pair of wells.

26. The thermal cycler apparatus of claim 25, wherein the first base plate and the second base plate are separated from each other by a space through which wires extending from the peltier plate may extend.

27. The thermal cycler apparatus of claim 1, wherein the peltier device is coupled to the well block by solder.

28. The thermal cycler apparatus of claim 1, further comprising:

a plurality of additional peltier devices, wherein each peltier device is thermally coupled to the heat sink wherein, the well block comprising a plurality of zones, each zone thermally coupled to its respective peltier device and each zone comprising one or more wells; and wherein each peltier device is individually driven to provide temperature uniformity to the wells.

29. The thermal cycler apparatus of claim 28, wherein each zone comprises 4 wells.

* * * * *